United States Patent
Uden et al.

(10) Patent No.: US 10,633,673 B2
(45) Date of Patent: *Apr. 28, 2020

(54) PRODUCTION METHODS

(71) Applicant: GLAXO GROUP LIMITED, Brentford, Middlesex (GB)

(72) Inventors: Mark Uden, Stevenage (GB); Ekaterini Kotsopoulou, Beckenham (GB)

(73) Assignee: GLAXO GROUP LIMITED, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/870,065

(22) Filed: Sep. 30, 2015

(65) Prior Publication Data
US 2016/0010111 A1    Jan. 14, 2016

Related U.S. Application Data

(63) Continuation of application No. 12/674,069, filed as application No. PCT/EP2008/060834 on Aug. 19, 2008, now Pat. No. 9,163,249.

(60) Provisional application No. 60/956,772, filed on Aug. 20, 2007.

(51) Int. Cl.
| | | |
|---|---|---|
| *C12N 15/85* | (2006.01) | |
| *C07K 16/00* | (2006.01) | |
| *C07K 16/18* | (2006.01) | |
| *C12N 7/02* | (2006.01) | |
| *C12N 15/67* | (2006.01) | |
| *A61K 39/12* | (2006.01) | |
| *A61K 39/00* | (2006.01) | |

(52) U.S. Cl.
CPC .............. *C12N 15/85* (2013.01); *A61K 39/12* (2013.01); *C07K 16/00* (2013.01); *C07K 16/18* (2013.01); *C12N 7/02* (2013.01); *C12N 15/67* (2013.01); *A61K 2039/525* (2013.01); *C07K 2317/41* (2013.01); *C07K 2317/56* (2013.01); *C12N 2770/24034* (2013.01); *C12N 2770/24051* (2013.01); *C12N 2800/60* (2013.01); *C12N 2830/40* (2013.01)

(58) Field of Classification Search
CPC ...................................................... C12N 15/85
See application file for complete search history.

(56) References Cited

U.S. PATENT DOCUMENTS

| 8,101,727 B2* | 1/2012 | Stover et al. .......... 530/388.22 |
| 9,163,249 B2* | 10/2015 | Uden ..................... C07K 16/00 |
| 2004/0148647 A1* | 7/2004 | Enenkel ................ C12N 15/65 800/14 |
| 2006/0057138 A1 | 3/2006 | Wood et al. |
| 2011/0142824 A1* | 6/2011 | Burbidge et al. ........... 424/133.1 |

FOREIGN PATENT DOCUMENTS

| EP | 0953639 | * 3/1999 | ............. C12N 15/13 |
| WO | WO 2002/076578 | 10/2002 | |
| WO | WO 2004/032868 | 4/2004 | |
| WO | WO 2004/046168 | 6/2004 | |
| WO | WO 2005/111623 A1 | 11/2005 | |
| WO | WO 2006/066089 | 6/2006 | |
| WO | WO 2006/081171 | 8/2006 | |
| WO | WO 2006/122822 | 11/2006 | |
| WO | WO 2007/068429 | 6/2007 | |
| WO | WO 2007/113172 | 10/2007 | |

OTHER PUBLICATIONS

Huang et al. J Immunol Methods 2007;322:28-39 Online Feb. 2007.*
Zhang et al. Biochim Biophys Acta 1997;1357:215-224.*
Nechansky et al. Molecular Immunology Mar. 2007;44:1815-1817.*
Wurm, Nat Biotech 2004;221393-8.*
Grote et al. Nucleic Acids Res 2005;33:W526-31.*
Gustafsson et al. Trends Biotech 2004;22:346-53.*
Massaer et al. (Int Arch Allergy Innnnunol 2001;125:32-43). (Year: 2001).*
Kalwy et al. Mole Biotech 2006;34:151-6.*
Bianchi et al. Biotech Bioengineer 2003;84:439-44.*
Werner et al. Acta Padiatri Suppl Apr. 2007;96:17-22.*
Pihlkala et al. Biochem Biophys Res Comm 2004;324:1165-72.*
Solomon et al. PNAS 1996;93:452-5.*
Invitrogen User Manual catalog No. v175-20.
Bebbington, et al., DNA cloning, vol. III, pp. 163-188, (1987).
Chishima, et al, PNAS, vol. 94, No. 21, Oct. 14, 1997, pp. 11573-11576.
Kotsopoulou, et al., Journal of Biotechnology, 146(2010)186-193.
Ludwig, et al., BioProcess International, vol. 4, No. 3, May 1, 2006, pp. 14-23.
Hu, et al., "Codon optimization, expression, and characterization of an internalizing anti-ErbB2 single-chain antibody in Pichia pastoris," *Protein Expression and Purification*, 47(1):249-257 (2006).
Carton, et al., Protein Expression and Purification, vol. 55, 2007, pp. 279-286.
Imai-Nishiya, et al., Bmc Biotechnol, vol. 7, 2007, p. 84.
Kanda, et al., Journal of Biotechnology, vol. 130,2007,pp. 300-310.
Nivitchanyang, et al., biotechnol bioeng, vol. 98,2007, pp. 825-841.

(Continued)

*Primary Examiner* — Scott Long
(74) *Attorney, Agent, or Firm* — Nicole Ginanni; Edward R. Gimmi

(57) ABSTRACT

The present invention provides methods of reducing the levels of a titratable selectable pressure required, the number of amplification cycles, and the time taken to generate protein expressing cell lines by altering the codons of the desired open-reading-frames. Through the use of codon adaptation for this purpose the methods of the invention consistently provide sufficient yields in faster time frames saving many weeks in cell line development activities. Furthermore the methods of the invention also generate cell lines with lower concentrations of selection and amplification agent than previously achievable. Accordingly lower levels of selection and amplification marker in the final cells lines are observed.

10 Claims, 15 Drawing Sheets

Specification includes a Sequence Listing.

(56) References Cited

OTHER PUBLICATIONS

Tey, et al., Biotechnol Bioeng, vol. 68, 2000, pp. 31-43.
Wurm, Nature Biotechnology, vol. 22, No. 11, 2004, pp. 1393-1398.
Yallop, et al., Modern Biopharmaceuticals, 2005, pp. 779-807.
Yamane-Ohnuki, et al., Biotech Bioeng, vol. 87, 2004, pp. 614-622.
Invitrogen User Manual, Catalog No. V175-20, 36 pages, (2010).
Sharp et al., "The codon adaptation index—a measure of directional synonymous codon usage bias, and its potential applications", *Nucleic Acids Research*, vol. 15, No. 3, pp. 1281-1295 (1987).

* cited by examiner

Figure 1.
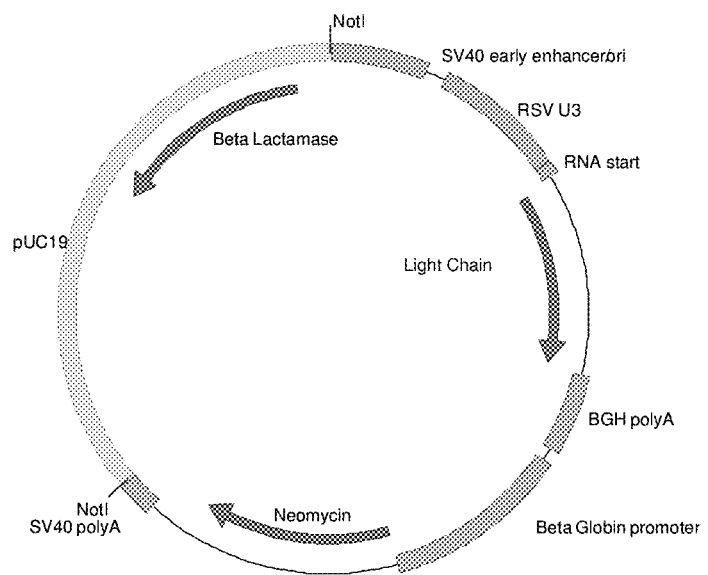
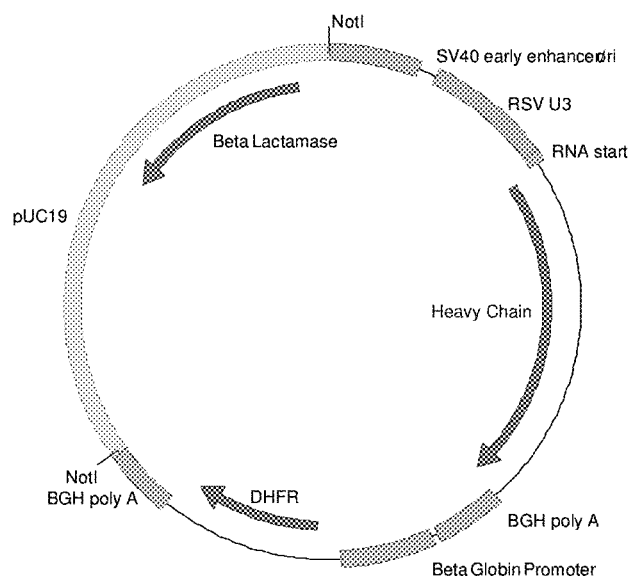

Figure 2.

ATGGAGTTGGGGCTGTGCTGGGTTTTCCTTGTTGCTATTTTAGAAGGTGTCCAG
TGTGAGGTGCAGCTGGTGGAGTCTGGGGGAGGCTTGGTACAGCCTGGGGGGT
CCCTGAGACTCTCCTGTGCAGTCTCTGGATTCACCTTCAGTGACAACGGAATGG
CGTGGGTCCGCCAGGCTCCAGGGAAGGGGCTGGAGTGGGTTTCATTCATTAGT
AATTTGGCATATAGTATCGACTACGCAGACACTGTGACGGGCCGATTCACCATC
TCCAGAGACAATGCCAAGAACTCACTGTATCTGCAAATGAACAGCCTGAGAGCC
GAGGACACGGCTGTGTATTACTGTGTCAGCGGGACCTGGTTTGCTTACTGGGG
CCAGGGCACACTAGTCACAGTCTCCTCAGCCTCCACCAAGGGCCCATCGGTCT
TCCCCCTGGCACCCTCCTCCAAGAGCACCTCTGGGGGCACAGCGGCCCTGGG
CTGCCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCA
GACCTACATCTGCAACGTGAATCACAAGCCCAGCAACACCAAGGTGGACAAGA
AAGTTGAGCCCAAATCTTGTGACAAAACTCACACATGCCCACCGTGCCCAGCAC
CTGAACTCGCGGGGGCACCGTCAGTCTTCCTCTTCCCCCCAAAACCCAAGGAC
ACCCTCATGATCTCCCGGACCCCTGAGGTCACATGCGTGGTGGTGGACGTGAG
CCACGAAGACCCTGAGGTCAAGTTCAACTGGTACGTGGACGGCGTGGAGGTGC
ATAATGCCAAGACAAAGCCGCGGGAGGAGCAGTACAACAGCACGTACCGTGTG
GTCAGCGTCCTCACCGTCCTGCACCAGGACTGGCTGAATGGCAAGGAGTACAA
GTGCAAGGTCTCCAACAAAGCCCTCCCAGCCCCATCGAGAAAACCATCTCCAA
AGCCAAAGGGCAGCCCCGAGAACCACAGGTGTACACCCTGCCCCCATCCCGG
GATGAGCTGACCAAGAACCAGGTCAGCCTGACCTGCCTGGTCAAAGGCTTCTA
TCCCAGCGACATCGCCGTGGAGTGGGAGAGCAATGGGCAGCCGGAGAACAAC
TACAAGACCACGCCTCCCGTGCTGGACTCCGACGGCTCCTTCTTCCTCTACAGC
AAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGT
CTCCGGGTAAA

Figure 3.

ATGAGGCTCCCTGCTCAGCTCCTGGGGCTGCTAATGCTCTGGGTCTCTGGATC
CAGTGGGGATATTGTGATGACTCAGTCTCCACTCTCCCTGCCCGTCACCCCTGG
AGAGCCGGCCTCCATCTCCTGCAGAGTTAGTCAGAGCCTTTTACACAGTAATGG
ATACACCTATTTACATTGGTACCTGCAGAAGCCAGGGCAGTCTCCACAGCTCCT
GATCTATAAAGTTTCCAACCGATTTTCTGGGGTCCCTGACAGGTTCAGTGGCAG
TGGATCAGGCACAGATTTTACACTGAAAATCAGCAGAGTGGAGGCTGAGGATGT
TGGGGTTTATTACTGCTCTCAAACTAGACATGTTCCGTACACGTTCGGCGGAGG
GACCAAGGTGGAAATCAAACGTACGGTGGCTGCACCATCTGTCTTCATCTTCCC
GCCATCTGATGAGCAGTTGAAATCTGGAACTGCCTCTGTTGTGTGCCTGCTGAA
TAACTTCTATCCCAGAGAGGCCAAAGTACAGTGGAAGGTGGACAACGCCCTCC
AATCGGGTAACTCCCAGGAGAGTGTCACAGAGCAGGACAGCAAGGACAGCACC
TACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGA
GCTTCAACAGGGGAGAGTGT

Figure 4.

```
ATGGAGCTCGGGCTGTGCTGGGTGTTCCTCGTGGCCATCCTGGAGGGAGTGCA
GTGTGAGGTGCAGCTGGTGGAGAGTGGGGGCGGCCTGGTGCAGCCCGGCGG
CAGCCTGCGGCTGTCGTGCGCCGTGAGCGGCTTCACCTTCAGTGACAACGGCA
TGGCTTGGGTCAGGCAGGCCCCGGAAGGGGCTCGAGTGGGTGAGCTTCAT
CAGTAACCTGGCCTACAGTATCGACTATGCTGACACCGTGACCGGCCGCTTCA
CTATCTCTCGGGATAATGCTAAGAACAGCCTGTACCTCCAGATGAACAGCCTGC
GCGCTGAGGACACCGCCGTGTACTACTGCGTGTCTGGAACCTGGTTCGCCTAC
TGGGGCCAGGGTACACTAGTCACAGTCTCCTCAGCCTCCACCAAGGGCCCATC
GGTCTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCT
CAGGACTCTACTCCCTCAGCAGCGTGGTGACCGTGCCCTCCAGCAGCTTGGGC
ACCCAGACCTACATCTGCAACGTGAATCACAAGCCCAGCAACACCAAGGTGGA
CAAGAAAGTTGAGCCCAAATCTTGTGACAAAACTCACACATGCCCACCGTGCCC
AGCACCTGAACTCGCGGGGGCACCGTCAGTCTTCCTCTTCCCCCCAAAACCCA
AGGACACCCTCATGATCTCCCGGACCCCTGAGGTCACATGCGTGGTGGTGGAC
GTGAGCCACGAAGACCCTGAGGTCAAGTTCAACTGGTACGTGGACGGCGTGGA
GGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATC
CCGGGATGAGCTGACCAAGAACCAGGTCAGCCTGACCTGCCTGGTCAAAGGCT
TCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCTCAT
GCTCCGTGATGCATGAGGCTCTGCACAACCACTACACGCAGAAGAGCCTCTCC
CTGTCTCCGGGTAAA
```

Figure 5.

ATGCGCCTGCCTGCCCAGCTGCTCGGCCTGCTGATGCTGTGGGTGTCGGGCA
GCTCCGGCGACATCGTCATGACCCAGAGCCCCCTGAGTCTCCCCGTCACCCCC
GGCGAACCTGCCAGCATCAGCTGCAGGGTGTCCCAGTCGCTGCTCCATTCCAA
CGGGTACACGTACCTGCATTGGTACCTGCAGAAGCCCGGGCAATCCCCTCAGC
TGCTGATCTACAAGGTGAGCAACCGCTTCTCCGGCGTCCCGGACCGGTTCAGT
GGCAGCGGCTCTGGAACCGACTTCACCCTGAAAATCAGCCGCGTGGAAGCTGA
GGACGTGGGCGTCTACTACTGCAGCCAGACCCGGCATGTGCCCTACACCTTCG
GCGGCGGCACAAAGGTGGAGATCAAGCGTACGGTGGCTGCACCATCTGTCTTC
ATCTTCCCGCCATCTGATGAGCAGTTGAAATCTGGAACTGCCTCTGTTGTGTGC
CTGCTGAATAACTTCTATCCCAGAGAGGCCAAAGTACAGTGGAAGGTGGACAAC
GCCCTCCAATCGGGTAACTCCCAGGAGAGTGTCACAGAGCAGGACAGCAAGGA
CAGCACCTACAGCCTCAGCAGCACCCTGACGCTGAGCAAAGCAGACTACGAGA
AACACAAAGTCTACGCCTGCGAAGTCACCCATCAGGGCCTGAGCTCGCCCGTC
ACAAAGAGCTTCAACAGGGGAGAGTGT

Figure 6.

```
ATGGAGCTGGGCCTGTGCTGGGTGTTCCTGGTGGCCATCCTGGAGGGCGTGC
AGTGCGAGGTGCAGCTGGTGGAGAGCGGCGGCGGCCTGGTGCAGCCCGGCG
GCAGCCTGCGCCTGAGCTGCGCCGTGAGCGGCTTCACCTTCAGCGACAACGG
CATGGCCTGGGTGCGCCAGGCCCCCGGCAAGGGCCTGGAGTGGGTGAGCTTC
ATCAGCAACCTGGCCTACAGCATCGACTACGCCGACACCGTGACCGGCCGCTT
CACCATCAGCCGCGACAACGCCAAGAACAGCCTGTACCTGCAGATGAACAGCC
TGCGCGCCGAGGACACCGCCGTGTACTACTGCGTGAGCGGCACCTGGTTCGC
CTACTGGGGCCAGGGCACACTAGTCACAGTCTCCTCAGCCTCCACCAAGGGCC
CATCGGTCTTCCCCCTGGCACCCTCCTCCAAGAGCACCTCTGGGGGCACAGCG
GCCCTGGGCTGCCTGGTCAAGGACTACTTCCCCGAACCGGTGACGGTGTCGTG
GAACTCAGGCGCCCTGACCAGCGGCGTGCACACCTTCCCGGCTGTCCTACAGT
CCTCAGGACTCTACTCCCTCAGCAGCGTGGTGACCGTGCCCTCCAGCAGCTTG
GGCACCCAGACCTACATCTGCAACGTGAATCACAAGCCCAGCAACACCAAGGT
GGACAAGAAAGTTGAGCCCAAATCTTGTGACAAAACTCACACATGCCCACCGTG
CCCAGCACCTGAACTCGCGGGGGCACCGTCAGTCTTCCTCTTCCCCCCAAAAC
CCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGT
GGAGGTGCATAATGCCAAGACAAAGCCGCGGGAGGAGCAGTACAACAGCACGT
ACCGTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGCCCC
CATCCCGGGATGAGCTGACCAAGAACCAGGTCAGCCTGACCTGCCTGGTCAAA
GGCTTCTATCCCAGCGACATCGCCGTGGAGTGGGAGAGCAATGGGCAGCCGG
AGAACAACTACAAGACCACGCCTCCCGTGCTGGACTCCGACGGCTCCTTCTTC
CTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCC
TCTCCCTGTCTCCGGGTAAA
```

Figure 7.

ATGCGCCTGCCCGCCCAGCTGCTGGGCCTGCTGATGCTGTGGGTGAGCGGCA
GCAGCGGCGACATCGTGATGACCCAGAGCCCCCTGAGCCTGCCCGTGACCCC
CGGCGAGCCCGCCAGCATCAGCTGCCGCGTGAGCCAGAGCCTGCTGCACAGC
AACGGCTACACCTACCTGCACTGGTACCTGCAGAAGCCCGGCCAGAGCCCCCA
GCTGCTGATCTACAAGGTGAGCAACCGCTTCAGCGGCGTGCCCGACCGCTTCA
GCGGCAGCGGCAGCGGCACCGACTTCACCCTGAAGATCAGCCGCGTGGAGGC
CGAGGACGTGGGCGTGTACTACTGCAGCCAGACCCGCCACGTGCCCTACACCT
TCGGCGGCGGCACCAAGGTGGAGATCAAGCGTACGGTGGCTGCACCATCTGT
CTTCATCTTCCCGCCATCTGATGAGCAGTTGAAATCTGGAACTGCCTCTGTTGT
GTGCCTGCTGAATAACTTCTATCCCAGAGAGGCCAAAGTACAGTGGAAGGTGG
ACAACGCCCTCCAATCGGGTAACTCCCAGGAGAGTGTCACAGAGCAGGACAGC
AAGGACAGCACCTACAGCCTCAGCAGCACCCTGACGCTGAGCAAAGCAGACTA
CGAGAAACACAAAGTCTACGCCTGCGAAGTCACCCATCAGGGCCTGAGCTCGC
CCGTCACAAAGAGCTTCAACAGGGGAGAGTGT

Figure 8.

ATGGAGCTGGGCCTGTGCTGGGTGTTCCTGGTGGCCATCCTGGAGGGCGTGC
AGTGCGAGGTGCAGCTGGTGGAGTCTGGCGGCGGACTGGTGCAGCCTGGCGG
CAGCCTGAGACTGAGCTGTGCCGTGTCCGGCTTCACCTTCAGCGACAACGGCA
TGGCCTGGGTGAGGCAGGCCCTGGCAAGGGCCTGGAGTGGGTGTCCTTCAT
CAGCAACCTGGCCTACAGCATCGACTACGCCGACACCGTGACCGGCAGATTCA
CCATCAGCCGGGACAACGCCAAGAACAGCCTGTACCTGCAGATGAACAGCCTG
AGAGCCGAGGACACCGCCGTGTACTACTGTGTGAGCGGCACCTGGTTCGCCTA
CTGGGGCCAGGGCACCCTGGTGACCGTGTCCAGCGCCAGCACCAAGGGCCCC
AGCGTGTTCCCCCTGGCCCCCAGCAGCAAGAGCACCAGCGGCGGCACAGCCG
CCCTGGGCTGCCTGGTGAAGGACTACTTCCCCGAACCGGTGACCGTGTCCTGG
AACAGCGGAGCCCTGACCAGCGGCGTGCACACCTTCCCCGCCGTGCTGCAGA
GCAGCGGCCTGTACAGCCTGAGCAGCGTGGTGACCGTGCCCAGCAGCAGCCT
GGGCACCCAGACCTACATCTGTAACGTGAACCACAAGCCCAGCAACACCAAGG
TGGACAAGAAGGTGGAGCCCAAGAGCTGTGACAAGACCCACACCTGCCCCCCC
TGCCCTGCCCCCGAGCTGGCCGGAGCCCCCAGCGTGTTCCTGTTCCCCCCCAA
GCCTAAGGACACCCTGATGATCAGCAGAACCCCCGAGGTGACCTGTGTGGTGG
TGGATGTGAGCCACGAGGACCCTGAGGTGAAGTTCAACTGGTACGTGGACGGC
GTGGAGGTGCACAATGCCAAGACCAAGCCCAGGGAGGAGCAGTACAACAGCA
CCTACCGGGTGGTGTCCGTGCTGACCGTGCTGCACCAGGATTGGCTGAACGGC
AAGGAGTACAAGTGTAAGGTGTCCAACAAGGCCCTGCCTGCCCCTATCGAGAA
AACCATCAGCAAGGCCAAGGGCCAGCCCAGAGAGCCCCAGGTGTACACCCTG
CCCCCTAGCAGAGATGAGCTGACCAAGAACCAGGTGTCCCTGACCTGCCTGGT
GAAGGGCTTCTACCCCAGCGACATCGCCGTGGAGTGGGAGAGCAACGGCCAG
CCCGAGAACAACTACAAGACCACCCCCCTGTGCTGGACAGCGATGGCAGCTT
CTTCCTGTACAGCAAGCTGACCGTGGACAAGAGCAGATGGCAGCAGGGCAACG
TGTTCAGCTGCTCCGTGATGCACGAGGCCCTGCACAATCACTACACCCAGAAG
AGCCTGAGCCTGTCCCCTGGCAAG

Figure 9.

ATGAGACTGCCCGCCCAGCTGCTGGGCCTGCTGATGCTGTGGGTGTCCGGCA
GCAGCGGCGACATCGTGATGACCCAGAGCCCCCTGAGCCTGCCCGTGACCCC
TGGCGAGCCCGCCAGCATCAGCTGTAGAGTGAGCCAGAGCCTGCTGCACAGC
AACGGCTACACCTACCTGCACTGGTATCTGCAGAAGCCTGGCCAGAGCCCTCA
GCTGCTGATCTACAAGGTGTCCAACCGGTTCAGCGGCGTGCCTGATAGATTCA
GCGGCAGCGGCTCCGGCACCGACTTCACCCTGAAGATCAGCAGAGTGGAGGC
CGAGGATGTGGGCGTGTACTACTGCTCCAGACCAGACACGTGCCTTACACCT
TTGGCGGCGGAACAAAGGTGGAGATCAAGCGTACGGTGGCCGCCCCAGCGT
GTTCATCTTCCCCCCCAGCGATGAGCAGCTGAAGAGCGGCACCGCCAGCGTGG
TGTGTCTGCTGAACAACTTCTACCCCGGGAGGCCAAGGTGCAGTGGAAGGTG
GACAATGCCCTGCAGAGCGGCAACAGCCAGGAGAGCGTGACCGAGCAGGACA
GCAAGGACTCCACCTACAGCCTGAGCAGCACCCTGACCCTGAGCAAGGCCGAC
TACGAGAAGCACAAGGTGTACGCCTGTGAGGTGACCCACCAGGGCCTGTCCAG
CCCCGTGACCAAGAGCTTCAACCGGGGCGAGTGC

Figure 10:
(A)
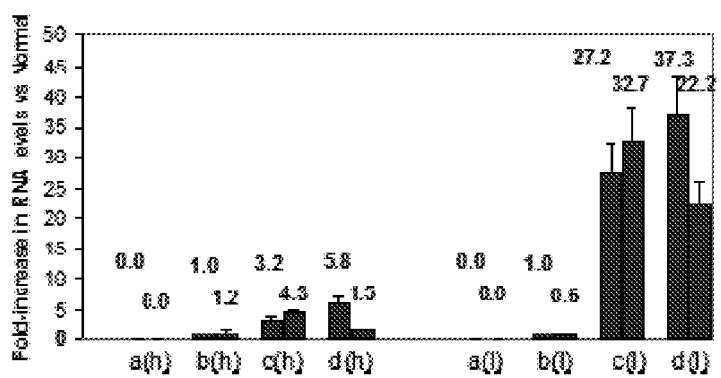
(B)
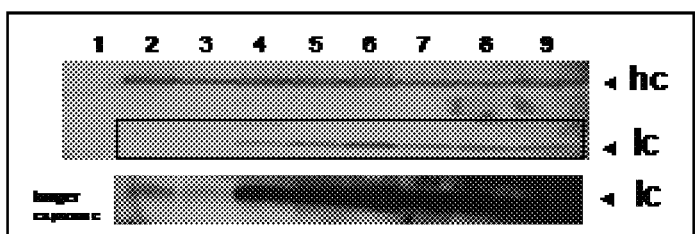
(C)
| Lane | 1 | 2 | 3 | 4 | 5 | 6 | 7 | 8 | 9 |
|---|---|---|---|---|---|---|---|---|---|
| Titre: | 4 | 9 | 8 | 345 | 142 | 174 | 190 | 583 | 423 |

Light Chain CDR1 of Project 5

AGA GTT AGT CAG AGC CTT TTA CAC AGT AAT GGA TAC ACC TAT TTA CAT    Original CAI    Project 5(a)
AGG GTG TCC CAG TCG CTG CTC CAT TCC AAC GGG TAC ACG TAC CTG CAT    High CAI        Project 5(c)
CGC GTG AGC CAG AGC CTG CTG CAC AGC AAC GGC TAC ACC TAC CTG CAC

(B)

Human codon preference in highly expressed genes (adapted from Massaer et al, Int Arch Allergy Immunol 2001: pp32-43)

```
Ala: GCC>GCT=GCG>GCA              Ile: ATC>ATT>ATA
Arg: CGC>CGG>AGG>AGA>CGT>CGA      Leu: CTG>CTC>TTG>CTT>CTA>TTA
Asn: AAC>AAT                       Lys: AAG>AAA
Asp: GAC>GAT                       Phe: TTC>TTT
Cys: TGC>TGT                       Pro: CCC>CCT>CCG>CCA
Gln: CAG>CAA                       Ser: AGC>TCC>TCT>AGT>TCG>TCA
```

(C)

Human codon preference adapted from The Codon Useage Database (89533 CD's)

```
Ala: GCC>GCT>GCG>GCA              Ile: ATC>ATT>ATA
Arg: AGA=AGG>CGG>CGC>CGA>CGT      Leu: CTG>CTC>TTG=CTT>TTA>CTA
Asn: AAC>AAT                       Lys: AAG>AAA
Asp: GAC>GAT                       Phe: TTC>TTT
Cys: TGC>TGT                       Pro: CCC>CCT>CCA>CCG
Gln: CAG>CAA                       Ser: AGC>TCC>TCT>AGT=TCA>TCG
Glu: GAG>GAA                       Thr: ACC>ACA>ACT>ACG
```

| | Production Model | %NGHC | Average* |
|---|---|---|---|
| Non-adapted Open Reading frames (Seq ID 10 and 11; CAI: HC 0.809, LC 0.761)<br>Host: CHO-K1<br>Vectors: pEE14.4/6.4 Vectors<br>Selection/Maintenance/Amplification: Glutamine withdrawal plus MSX<br>Media: CD-CHO (Invitrogen)<br>Feed: Non-animal hydrolysate (Day 4)<br><br>One clone (chosen on titre) is the only clone for which NGHC data was generated: | Clone 1 Shake Flask<br>Clone 1 5-Litre<br>Clone 1 80-Litre (1)<br>Clone 1 80-Litre (2)<br>Clone 1 80-Litre (3)<br>Clone 1 80-Litre (4)<br>Clone 1 1000-Litre (1)<br>Clone 1 1000-Litre (2) | 1<br>2.3<br>14.5<br>5.5<br>6.1<br>4.6<br>12.4<br>8.3 | 6.8 |
| Project 5(a): Non-adapted open reading frames (CAI: HC 0.809, LC 0.761)<br>Host: CHO-DG44<br>Vectors: RLN/RLD<br>Selection/Maintenance/Amplification: G418, nucleoside withdrawal plus MTX<br>Media: G70 (GSK)<br>Feed: None<br><br>Clone 1,2,3 and 4 (chosen on titre) are the clones for which NGHC data was generated | Clone 1 Shake Flask<br>Clone 2 Shake Flask<br>Clone 3 Shake Flask<br>Clone 4 Shake Flask | 4.7<br>10.9<br>2.3<br>7.7 | 6.4 |
| Project 5(c): Adapted open reading frames (CAI : HC 0.872, LC 0.894)<br>Same vector backbones, cell line development protocols and media as project 5A<br><br>Clones 1,2 and 3 (chosen on titre) are the clones for which NGHC data was generated | Clone 1 Shake Flask<br>Clone 2 Shake Flask<br>Clone 3 Shake Flask<br>Clone 3 Shake Flask (Repeat)<br>Clone 3 2-Litre Reactor | 1.5<br>0.8<br>2.3<br>1.7<br>1.6 | 1.6 |
| Project 5(d): Adapted open reading frames (CAI: HC 0.982, LC 0.976)<br>Same vector backbones, cell line development protocols and media as project 5A<br><br><br>Clones 1,2,3 & 4 (chosen on titre) are the clones for which NGHC data was generated<br>Best Clone (clone 1 (O97-7) scaled to 1000-Litre to supply clinical trial material | Clone 1 Shake Flask<br>Clone 1 Shake Flask (Repeat)<br>Clone 2 Shake Flask<br>Clone 3 Shake Flask<br>Clone 4 Shake Flask<br>Clone 1 2-Litre<br>Clone 1 80-Litre<br>Clone 1 1000-Litre | 1.4<br>1.3<br>1.1<br>1.1<br>1<br>1.8<br>1.9<br>1.3 | 1.4 |
| *Average for each process. Note different processes have differing levels of clone and/or scale data. | | | |

(B)

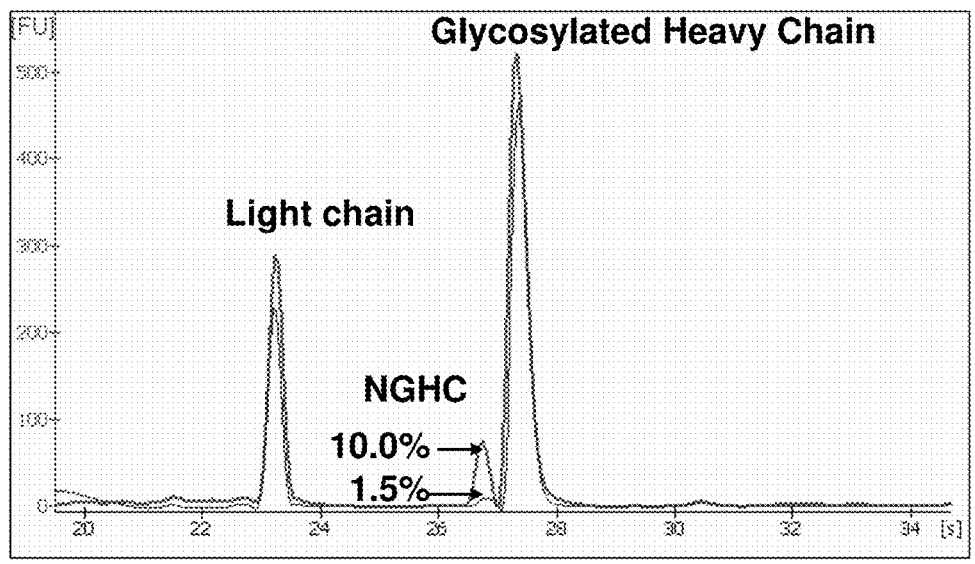

(A) Figure 14.
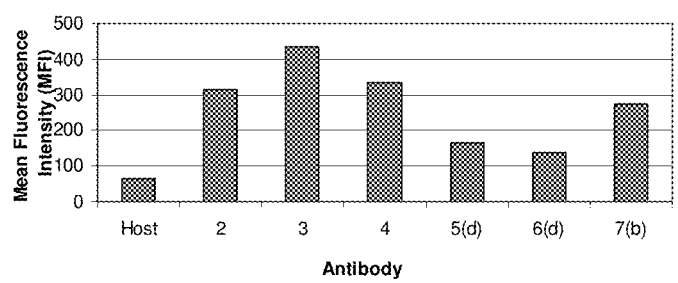
(B)
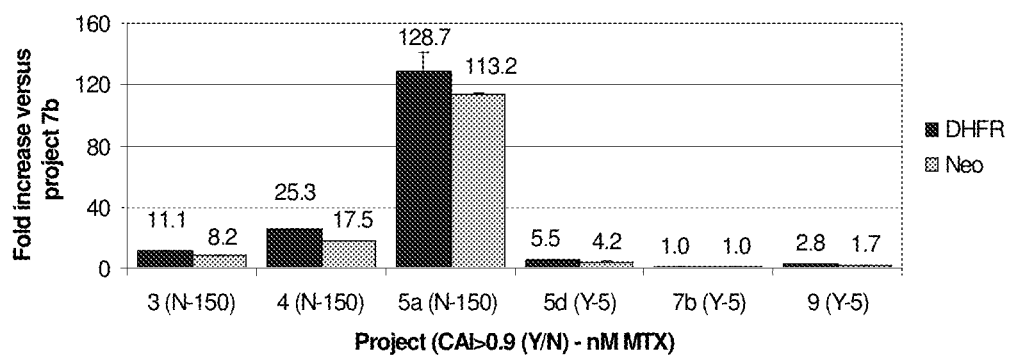

PRODUCTION METHODS

The present invention provides a method for producing a cell line which is capable of secreting a therapeutic protein. The method comprises the use of codon adapted gene sequences which results both in reduced protocol timelines and a decrease in the concentrations of antifolate required when generating eg. antibody producing cell lines via a selection and amplification system.

Mammalian cells such as CHO (Chinese Hamster Ovarian cells), NS0 and PerC6 cells are routinely employed within the biopharmaceutical industry to manufacture biopharmaceuticals. These cells are genetically engineered and then selected in such a way as to ensure that high titre expression of the desired protein is observed when the resulting cell lines are cultured in bioreactors.

Currently there are a number of methods to engineer and then select the best cells for this purpose. Often these methods involve 'amplification' to increase copy number of the integrated expression vector or vectors to improve yields observed of the desired protein. These 'amplification' methods are well described previously by Bebbington and Hentschel (DNA Cloning Volume III (IRL press, 1987)). The authors explain that a number of selectable markers (which are often in the form of nucleic acid sequences encoding enzymes involved in metabolism and essential for the host cells survival under certain culture media conditions) can be operatively linked to expression vectors designed to express the desired protein such that upon selection for the selectable marker, one also selects for expression of the desired protein. However because after such selection, the resulting titres of the desired protein are typically not sufficiently high, the selected cells are also subjected to 'amplification' regimes. These regimes normally involve subjecting the cells to certain toxic drugs that inhibit the selectable marker. Through such inhibition, populations of cells will be selected that have increased expression levels of this marker. Often this leads to increased expression levels of the operatively linked expression cassettes as well. Such increased expression or 'amplification' normally occurs due to genomic rearrangements resulting in increased copy number of selectable marker and operatively linked expression cassettes. Often through such 'co-amplification', titres are sufficiently improved to employ the resulting best clones to produce suitably high levels of the desired protein or proteins. When the vector copy number in individual cells subjected to amplification regimes have been further investigated, it has been observed that up until a 'plateau' of protein production is approached, the levels of production observed are typically proportionate to the increase in gene copy number (Bebbington and Hentshcel ibid).

Many different selectable markers suitable for amplification and so termed amplifiable selection markers have been identified to date. Each identified also has an associated 'selection and amplification' agent added to the cell culture media during selection and amplification regimes. Examples of such selectable marker/agent combinations include: adenosine deaminase/deoxycoformycin, aspartate transcarbamylase/N (phosphoacetyl)-L-aspartate, dihydrofolate reductase/methotrexate, glutamine synthetase/methionine sulphoximine, metallthionein-I/heavy metal, multi-drug resistance/adriamycin (see Bebbington and Hentschel ibid, Kellems 1991; Current Opinion in Biotechnology 2: pp 723-729). Additionally, it is more recently reported that antibiotic selection markers such as those conferring resistance to neomycin/G418 and zeocin can also be sometimes employed to increase copy number and so on occasion have been used as selection and amplification markers when combined with the appropriate cognate selection and amplification (antibiotic-based) selectable agent (e.g. Sauttle and Enenkel: Biotech Bioeng 2004 89 pp 530-538, and Kwaks et al: Nature Biotech 2003; 21; pp 553-558)

Whilst there are a number of methods to select the best genetically engineered cells for this purpose, the two most commonly used selection pressures are the glutamine synthetase (GS) and dihydrofolate reductase (DHFR) based selection methods.

The GS method involves operatively linking a glutamine synthetase expression cassette to that of the therapeutic protein expression cassette or cassettes. The subsequent operatively linked vectors are delivered to cells and vector chromosomal integration is selected for by depletion or withdrawal of glutamine from the media in which the cells are cultured. Addition of the glutamine synthetase inhibitors such as methionine sulfoximine (MSX) is often added to the culture media in order to ensure glutamine synthetase activity above and beyond that of endogenous host cell levels is selected for. The alternative DHFR selection method involves operatively linking a DHFR selection pressure to that of the therapeutic protein expression cassette or cassettes. The operatively linked vectors are delivered to cells and vector chromosomal integration selected for by withdrawal or depletion of nucleosides (e.g. hypoxanthine and thymidine). Typically for the DHFR method, it is commonplace to employ DHFR-negative host strains such as CHO DG44 or CHO DUX-B11. It is also commonplace to employ selection and amplification agents such as methotrexate (MTX).

The addition or stepwise titration of increasing amounts of the MSX or MTX selection and amplification agents in the respective GS and DHFR selection systems is often undertaken in order to augment expression by increasing gene copy number. Such methods can involve the addition of the selection and amplification agent to the cell culture directly. Alternatively the agent can be added to the growth media prior to the media being used in such cell culture. This addition or titration of such agents direct to either cell cultures, or media then used for cell culture is typically termed 'amplification'. For example in the GS system, MSX levels can be added or increased up to and beyond 500 µM whilst for the DHFR system, MTX antifolate levels can be added or increased up to and beyond 1 µM concentration levels. By use of such agents in this way followed by a culture period to allow the selection of cells that grow in the new concentration of selection agent, (each concentration step being termed a "round" of amplification), it has been shown that the area of the genome harbouring the selection pressure can also amplify thereby increasing the copy number of the selectable marker. Consequently when the selectable marker is operatively linked to the therapeutic protein expression cassettes, these cassettes may also amplify. By the use of appropriate selection and amplification agents when using the GS and DHFR selection system, yields of desired proteins can be significantly improved up until a 'production plateau' is approached (see Bebbington and Hentschel (ibid)). As a consequence, the clones that grow through such selection and amplification are then screened on titre/yield and the best clones are selected and further evaluated. From such titration and screening it is typical to identify and then commit to one clone for subsequent production of the desired protein or proteins.

Typically both the number of 'rounds' of amplification and the concentration of selection and amplification agent employed are not set or fixed in selection and amplification protocols. Instead it is typical for selection and amplification regimes to become progressively stringent up to a point in which a production threshold or plateau is approached. Specifically, when expressing antibodies, we and others have observed that clones approaching this plateau produce final titres in current extended unfed batch culture models and production bioreactors in the range of 0.3 g to 1.5 g per litre. This typically translates into cell productivities (Qp) in the range of 10-100 pg/cell/per day during such unfed batch culture conditions. However it is well known that whilst Qp (in pg/cell/per day terms) is important, it is not an exclusive determinant of productivity as clones with the highest Qp do not always give rise to the highest volumetric titres. For a recent review see Wurm 2004; Nature Biotechnology Vol 22; pp 1393-1398.

Selection and amplification methods have been employed successfully to generate cell lines used in manufacturing campaigns to make desired proteins used in clinical trials. However whilst the titres generated by selection and amplification methodology are sufficient, such methods are still undesirable for a number of reasons including time, cost and safety. For example, the titration of amplification and selection agents in cell line 'amplification' protocols delays clone selection and colony outgrowth, each round of amplification taking a month or more to complete. Second, selection and amplification agents like methotrexate and methionine sulfoximine are toxic chemicals which must be removed if it is to be used therapeutically. Third, selection and amplification agent resistance can occur in mammalian cells which can result in less stringent selection pressure and result in clonal and product yield instability. Fourth, amplification can occasionally occur episomally. Such episomes and any operatively linked functional expression cassettes are not always inherited equally during cell division leading to increased variation and instability in culture. Fifth, the genome rearrangements generated during amplification protocols can result in significant changes to the host cell genome leading to variable phenotypes in resulting clones. Sixth, selection and amplification agent by-products, such as polyglutamated methotrexate can inhibit additional functions of the cells (e.g. Allegra et al 1985 J Biological Chem 260; 17 pp 9720-9726). Seventh, many of these selection and amplification agents are also potentially toxic to the operators involved with culturing cells and running the bioreactors if they are exposed to high levels. Eighth, it has also been observed that increasing the copy number of integrated expression vectors in mammalian host cells can result in increased repeat-induced-gene-silencing (RIGS) activity by the host cell which can ultimately result in a reduction in expression levels from each of the integrated expression vectors (eg see McBurney M W et al Exp Cell Res 2002 274:1-8).

Consequently, it would be highly desirable to employ the selection and amplification methodology with reduced levels of selection and amplification agent in a reduced number of rounds of amplification whilst still achieving the same final yield of the therapeutic protein, such that the time taken to generate the final cell line is faster and/or the level of the undesirable toxic agent needed to generate the final line is reduced or entirely excluded during cell line generation, selection and culture (M. Celina de la Cruz Edmonds et al (Mol Biotechnology 2006 34:179-190).

With 64 triple base-pair codon combinations but only 20 amino acids, it has been known for many decades that there is redundancy in the genetic code. However, the use of codon bias to augment expression was not realised until the 1980s. For example, in 1982 Bennetzen and Hall (J Biol Chem 257 pp 3026-3031) observed species specific codon bias in strongly expressed genes of both prokaryotes and eukaryotes. They also noted that this bias was taxonomically divergent. As a consequence it was soon realised that one could modify the codon usage of open reading frames such to increase expression in recombinant expression systems. For example Kotula and Curtis (Biotechnolgy NY (1991) 9: 1386-9)) achieved significantly improved expression of a mammalian antibody light chain in yeast by codon adaptation of the open reading frame such to bias the codon usage towards those codons preferred by highly expressed endogenous yeast genes. Another very notable example was the codon adaptation of the green fluorescent protein to improve expression in mammalian cells (Zolotukhin S J Virol (1996) 70: 4646-54 and Yang et al Nucleic Acids Res 1996 24:4592-3).

Recent data suggest that by raising the codon adaptation index (CAI) score of open reading frames encoding antibody heavy and light chains, one can marginally improve production yields in mammalian host cells when the resulting adapted expression cassettes are operatively linked to the glutamine synthetase selectable markers and when the cells are incubated with the MSX selection and amplification agent. This data (presented at the IBC 2005 Cell Line Development and Engineering Conference), suggested that whilst mean expression levels were not significantly improved, the median positive clone in a group did increase marginally (from 37.8 µg/ml to 51.3 µg/ml) but only when both the heavy and light chain open reading frames were codon adapted. More recently M. Celina de la Cruz Edmonds et al (ibid), also recognised the desire to reduce the levels of selection and amplification agent when generating engineered cell lines expressing desirable proteins with aid of selection and amplification regimes. They demonstrated that through modification of the seeding density of transfected cells, one can reduce the levels of MSX employed, and reduce the number of weeks required to generate and maintain genetically engineered cell lines expressing equivalent or greater levels of the desired protein.

Recent published work has investigated the approaches of codon optimisation combined with the use of the glutamine synthetase selectable marker. For example the work presented by Kawley et al (Molecular Biotechnology 2006 Vol 34; pp 151-156), evaluates the impact of codon adaptation on the subsequent expression levels generated however, the results reported suggest only minor improvements in expression levels achieved.

Even more recently Carton et al (Protein Expression and Purification 55 (2007) pp 279-286) also investigated the impact of codon optimisation. Their work involved part codon optimisation of heavy and light chain antibodies open reading frames by various approaches. These modified coding sequences were then expressed in myeloma cells as mini-gene formats (ie containing introns) in expression cassettes operatively linked to the gpt selectable marker. No amplification approaches were discussed.

There is a need in the art to reduce the levels of selection and amplification agents required when employing expression systems operatively linked to amplifiable selection markers.

STATEMENT OF INVENTION

The present invention provides methods of reducing the levels of a titratable selectable pressure required, the number of amplification cycles, and the time taken to generate protein expressing cell lines by altering the codons of the desired open-reading-frames. Through the use of codon adaptation for this purpose the methods of the invention consistently provide sufficient yields in faster time frames saving many weeks in cell line development activities. Furthermore the methods of the invention also generate cell lines with lower concentrations of selection and amplification agent than previously achievable. Accordingly lower levels of selection and amplification marker in the final cells lines are observed.

The present invention provides methods to produce a cell line producing a therapeutic protein comprising the steps of:
a) obtaining a first polynucleotide sequence that encodes said therapeutic protein,
b) altering the first polynucleotide sequence to obtain a second polynucleotide sequence, wherein the codon adaptation index of the second polynucleotide sequence is greater than that of the first polynucleotide sequence and the first polynucleotide and second polynucleotide encode the same therapeutic protein.
c) transforming at least one cell with the second polynucleotide sequence of step (b) and a third polynucleotide sequence that encodes a selection marker which is capable of providing amplification of the second polynucleotide sequence within said cell,
d) growing said at least one cell of step (c) to create a first cell line comprising a plurality of cells, in medium that contains a concentration of a selection agent that inhibits the growth of cells in said cell line which express insufficient levels of the selection marker encoded by the third polynucleotide of step (c), such that the plateau of production of the protein encoded by the second polynucleotide is reached with fewer rounds of amplification and/or is reached at a lower concentration of selection agent than would be necessary to reach an equivalent plateau of production of said protein produced in a cell line transformed with the first polynucleotide.

In all the comparative methods as herein described unless stated otherwise all other parameters such as amplification protocols or concentrations of selection agents remain constant.

In one embodiment of the present invention the first cell line is cultured in bioreactors and the therapeutic protein produced is purified.

In one embodiment of the present invention the codon adaptation index of the second polynucleotide sequence is greater than 0.9, in a further embodiment the codon adaptation index of the second polynucleotide sequence is greater than 0.91, in yet a further embodiment the codon adaptation index of the second polynucleotide sequence is greater than 0.92, in yet a further embodiment the codon adaptation index of the second polynucleotide sequence is greater than 0.95.

In another embodiment of the present invention the level of selective agent required to achieve the arithmetic equivalency of therapeutic protein production yield is reduced to less than 50% when compared to the amount of selective agent used for the same method using the first polynucleotide sequence. In a further embodiment the level of selective agent is reduced to less than 25% when compared to the amount of selective agent used for the same method using the first polynucleotide sequence, in yet a further embodiment the level of selective agent is reduced to less than 5% when compared to the amount of selective agent used for the same method using the first polynucleotide sequence in yet a further embodiment the level of selective agent is reduced to less than 3% when compared to the amount of selective agent used for the same method using the first polynucleotide sequence.

In one embodiment of the present invention there is provided a method to produce a cell line producing a therapeutic protein comprising the steps of:
a) obtaining a first polynucleotide sequence that encodes a therapeutic protein and which possesses a codon adaptation index score of less than 0.9.
b) obtaining a second polynucleotide sequence that encodes a therapeutic protein wherein the codon adaptation index of the polynucleotide sequence is greater than 0.9.
c) transforming a cell line with the second polynucleotide sequence that encodes the therapeutic protein and a third polynucleotide sequence that encodes a selection marker which is capable of providing amplification of the second polynucleotide,
d) growing said at least one cell of step (c) to create a first cell line comprising a plurality of cells, in medium that contains a concentration of a selection agent that inhibits the growth of cells in said cell line which express insufficient levels of the selection marker encoded by the third polynucleotide of step (c), such that the plateau of production of the protein encoded by the second polynucleotide is reached with fewer rounds of amplification and/or is reached at a lower concentration of selection agent than would be necessary to reach an equivalent plateau of production of said protein produced in a cell line transformed with the first polynucleotide.

In one embodiment of the present invention the cell line to be transformed is metabolically deficient due to disruption or inhibition of an endogenous cellular enzyme.

In a further embodiment of the present invention the cell line to be transformed is deficient in a nucleoside synthesis pathway.

In one embodiment of the present invention the therapeutic protein is an antibody, a derivative thereof or an antigen binding fragment.

In one embodiment of the present invention the therapeutic protein is a monoclonal antibody.

In one embodiment of the present invention the selection marker is a polynucleotide encoding Dihydrofolate reductase (DHFR) and the selection agent is an antifolate. In a further embodiment the antifolate is methotrexate.

In another embodiment of the present invention the selection marker is a polynucleotide encoding Glutamine synthetase and the selection agent is methionine sulfoximine.

In one embodiment of the present invention only one round of amplification is required to achieve a plateau of protein production.

In one embodiment of the present invention the final yield of therapeutic protein is greater than 0.3 g/L in an unfed batch, in a further embodiment the final yield is greater than 0.5 g/L in an unfed batch, in yet a further embodiment the final yield is greater than 0.8 g/L in an unfed batch.

In another embodiment of the present invention the concentration of MTX used is less than 50 nM or less than 25 nM or less than 10 nM. In a further embodiment of the present invention the concentration of MTX used is 5 nM In another embodiment of the invention, only one amplification step, and so only one concentration of the selection and amplification agent, is required in the cell culture medium to achieve a plateau of protein production in the cells that are selected in said culture medium.

In one embodiment of the present invention there is provided an antibody produced by the method of the invention. In a further embodiment there is provided an antibody produced by this method wherein the antibody produced comprises at least one heavy chain and which has less than or equal to 5% of non-glycosylated heavy chain. In a further embodiment the antibody's heavy chain is 95% glycosylated, or is 96% glycosylated, or is 97% glycosylated, or is 98% glycosylated, or is 99% glycosylated. In yet a further embodiment the antibody is 100% glycosylated. In one embodiment of the present invention the highly glycosylated antibody is a monoclonal antibody. In a further embodiment the highly glycosylated antibody is an anti-ß-amyloid antibody. In yet a further embodiment the antibody has a heavy chain sequence of SEQ ID 18 and a light chain sequence of SEQ ID NO.19.

In another embodiment of the present invention there is provided an antigen binding fragment according to the invention described herein wherein the fragment is a Fab, Fab', F(ab')$_2$, Fv, bispecific, diabody, triabody, tetrabody, miniantibody, minibody, isolated variable heavy chain region or isolated variable light chain region, serum derived proteins (e.g. growth factors, cytokines, albumins etc) or combinatorial fusion thereof.

In another embodiment of the invention there is provided a stably transformed host cell comprising a vector comprising one or more expression cassettes encoding a heavy chain and/or a light chain of the antibody or antigen binding fragment thereof as described herein. For example such host cells may comprise a first vector encoding the light chain and a second vector encoding the heavy chain. Alternatively such expression cassettes can be combined prior to delivery.

In another embodiment of the present invention there is provided a host cell according to the invention described herein wherein the cell is eukaryotic, for example where the cell is mammalian. Examples of such cell lines include Chinese Hamster Ovary, BHK, HEK-293, NSO or PerC6. (for recent review see Wurm 2004: Nature Biotechnology 22; 11 pp 1393-1398). Such host cells may also contain advantageous genotypic and/or phenotypic modifications e.g. the CHO-DG44 host strain has copies of its dhfr gene disabled whilst other hosts might have the glutamine synthetase genes disabled. Alternative modifications may be to the enzyme machinery involved in protein glycosylation (e.g., Yamane-Ohnuki et al, Biotech Bioeng 2004 87: pp 614-622, Kanda et al, Journal of Biotechnology, 2007 130: pp 300-310, Imai-Nishiya et al BMC Biotechnol, 2007 7:84). Yet others may have advantageous genotypic and/or phenotypic modifications to host apoptosis, expression and survival pathways (e.g. Tey et al Biotechnol Bioeng 2000 68: 31-43, Yallop et al Modern Biopharmaceuticals 2005 Chapter 3 pp 779-807, Nivitchanyang et al Biotechnol Bioeng 2007 98:825-41, Figueroa et al Biotechnol Bioeng 2007 97:87-92). These and other modifications of the host alone or in combination, can be generated by standard techniques such as over-expression of non-host or host genes, gene knock-out approaches, gene silencing approaches (eg siRNA), or evolution and selection of substrains with desired phenotypes. Such techniques are well established in the art.

In another embodiment of the present invention there is provided a method for the production of a therapeutic protein according to the invention described herein which method comprises the step of culturing a host cell in a culture media, for example serum-free culture media.

In another embodiment of the present invention there is provided a method according to the invention described herein wherein said therapeutic protein is further purified to at least 95% or greater (e.g. 98% or greater) with respect to said antibody containing serum-free culture media.

In one embodiment of the invention there is provided mammalian expression vectors containing open reading frames that possess CAI scores above 0.9 and which encode antibodies, antibody related polypeptides, or derivatives or fusions thereof.

In another embodiment there is provided a first cell line transformed with a second polynucleotide sequence having a codon adaptation index that is greater than a first polynucleotide sequence wherein the first polynucleotide and second polynucleotide encode the same therapeutic protein and further comprising a third polynucleotide sequence that encodes a selection marker which is capable of providing amplification of the first polynucleotide sequence, wherein said first cell line produces a higher yield of said therapeutic protein compared with a second said cell line transformed with said first polynucleotide encoding said therapeutic protein when grown in selectable medium.

In a further embodiment there is provided a second cell line transformed with a second polynucleotide sequence that encodes a therapeutic protein and has a codon adaptation index that is greater than 0.9 and further comprising a third polynucleotide sequence that encodes a selection marker which is capable of providing amplification of a second polynucleotide sequence, wherein said second cell line produces a higher yield of said therapeutic protein compared with a first said cell line transformed with a first polynucleotide encoding said therapeutic protein wherein said first polynucleotide has a codon adaptation index that is less than 0.9 when grown in selectable medium.

In one embodiment of the present invention the CAI score of above 0.9 is calculated using the EMBOSS CAI scoring metric as described in Table 6.

In another embodiment of the present invention there is provided a cell line comprising a vector or an expression cassette according to the previous embodiments as described herein.

In yet a further embodiment there is provided a cell line or its progeny obtainable by the methods of the present invention.

In another embodiment of the present invention there is provided mammalian cells with genomes containing integrated or episomally maintained open reading frames that possess CAI scores above 0.9 (derived using the EMBOSS codon usage table E.human.cut) which encode for antibodies, antibody related polypeptides or derivatives thereof.

Throughout the present specification and the accompanying claims the term "comprising" and "comprises" incorporates "consisting of" and "consists of". That is, "comprising" and "comprises" are intended to convey the possible inclusion of other elements or integers not specifically recited, where the context allows.

Throughout the present specification and the accompanying claims the term "plateau of production" means the level of expression approached in extended unfed batch cultures whereby additional rounds of amplification typically produce less than a 2-fold increase relative to the parental amplified clone. When clones are engineered specifically to produce antibodies, clones producing between 0.3 g to 1.5 g per litre in standard extended unfed production cultures can typically be considered as approaching this plateau of production when using current unfed extended culture regimes and media recipes.

Single-cell sub-cloning of final clones approaching a production plateau can be undertaken by many standard methods including flow sorting (e.g. depositing a cell per well in a 96-well plate), soft-agar colony picking, or limiting dilution cloning. To ensure single-cell outgrowth in recipient wells, sometimes conditioned media or temporary feeder cultures should also be employed to support growth of the deposited otherwise lone cell. If live feeder co-cultures are required, then these can readily comprise parental host cells without integrated selectable vectors as such host cells can then be selected against once the deposited single cell clone begins dividing healthily.

The term open reading frame (ORF) as used throughout this specification refers to the nucleic acid coding sequence encoding a desired polypeptide chain or chains. The codons contained within such ORF coding sequences can be contiguous or alternatively they can contain introns. When included, such introns or intervening sequences are then typically removed via splicing reactions in the host cell prior to formation of the final, contiguous open reading frame in the mature mRNA.

The "yield" as used throughout this specification refers to the concentration of a product (e.g., heterologously expressed polypeptide) in solution (e.g., culture broth or cell-lysis mixture or buffer) and it is usually expressed as mg/L or g/L. An increase in yield may refer to an absolute or relative increase in the concentration of a product produced under two defined set of conditions.

The term operatively linked refers to the use of selectable and amplification markers employed to select host cells containing expression cassettes expressing desired protein products. This can be achieved by cloning the selectable and amplification marker into the same plasmid or vector as that containing the expression cassette expressing the desired protein or alternatively can be delivered to the cell on a separate plasmid or vector.

BRIEF DESCRIPTION OF FIGURES

FIG. 1: A schematic representation of the RSV promoter based vectors used in project 2, 3, 4, 5, 6 (a), 6 (b) and 7 (a). For the EF-1 alpha promoter based evaluations (of project 6 and 7) the RSV promoter was replaced with a human EF-1 alpha derived promoter plus first intron (see Kim D W Gene 1990 91: 217-23). This was obtained via PCR from human genomic DNA. This EF-1 alpha promoter was then cloned in these vectors in place of the RSV based promoter FIG. 2: Non-adapted heavy chain of project 5 with a CAI score of 0.809 and employed in project 5 (a) SEQ ID NO 10

FIG. 3: Non-adapted light chain of project 5 with a CAI score of 0.761 and employed in project 5 (a) SEQ ID NO 11

FIG. 4: Heavy Chain ORF of project 5 (b) with increased CAI score (0.847). See Table 5. See SEQ ID 12

FIG. 5: Light Chain ORF of project 5 (b) with increased CAI score (0.833). See Table 5. See SEQ ID 13

FIG. 6: Heavy Chain ORF of project 5 with increased CAI score (0.872). This sequence was employed in antibody project 5 (c). See SEQ ID NO 14.

FIG. 7: Light Chain ORF of project 5 with increased CAI score (0.894). This sequence was employed in antibody project 5 (c). See SEQ ID NO 15.

FIG. 8: Heavy Chain ORF of project 5 with increased CAI score (0.982). This sequence was employed in antibody project 5 (d). See also SEQ ID 16.

FIG. 9: Light Chain ORF of project 5 with increased CAI score (0.976). This sequence was employed in antibody project 5 (d). See also SEQ ID 17

FIG. 10: Heavy-chain and light-chain RNA and protein levels for antibody project 5.

FIG. 11: Codon Adaptation Methodology in Detail

FIG. 12: Example Product NGHC data obtained during project 5 final clone selection.

FIG. 14: Relative levels of DHFR gene copy and protein and Neo gene copy observed in engineered cells in various projects.

DETAILED DESCRIPTION

Figure 13:
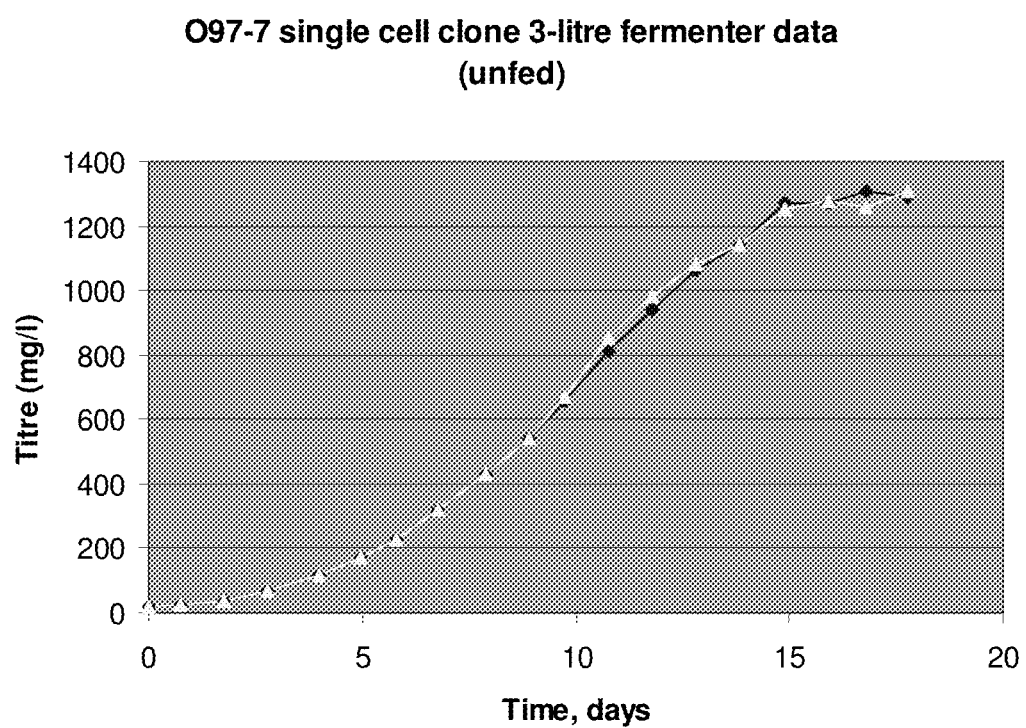
FIG. 13: Example titre generated from 097-7 (project 5 (d), 5 nM MTX chosen clone CAI HC 0.982, LC 0.976) with approximately 3-months additional development work after final cell-line amplification and selection.
Figure 15:
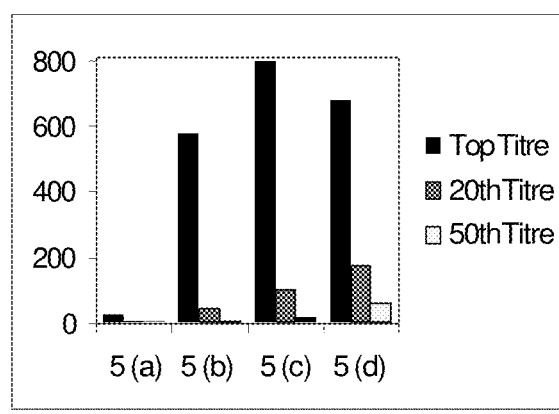
FIG. 15: Depicts the average results for Top, $20^{th}$ and $50^{th}$ titres.

The codon usage frequency of the genes encoding the therapeutic polypeptides produced according to the present invention is measured and defined by codon adaptation index (CAI).

Codon adaptation is the adaptation of the codons of an open reading frame to the synonymous codons preferred in human/mammalian genes whilst avoiding the introduction of unwanted secondary sequence functions that impede expression of the resulting open reading frames. We have observed that preferred human codons are also very suitable even when subsequent expression is planned in non-human mammalian cells (e.g. hamster derived cells). However, if the most preferred codon for any given amino acid differs in a given mammalian species then this can also be employed instead of the human preference. The "CAI score" generated for each open reading frame highlights the degree the open reading frame is adapted to the use of synonymous codons most preferred by human/mammalian genes.

Within the context of the present invention, a CAI score of 1 means that the most optimal codon is used for each amino acid in each codon position. For optimal results in the methods of the present invention the genes encoding the therapeutic protein have a CAI which is sufficiently close to 1 such that the desired level of expression of the therapeutic protein is achieved with significantly less selection and amplification agent and/or in a faster time relative to that observed when expressing the naturally occurring starting sequence, for example, the CAI is at least 0.9, or at least 0.95 or at least 0.975.

It is however not necessary to replace all codons with most preferred codons, or replace all least preferred with more preferred codons. The only requirement is that the resulting sequence possesses an unnaturally high CAI score and does not contain expression disrupting elements. Commercially available software such as Leto 1.0 (Entelechon, Regensburg, Germany) can design a sequence of suitably high CAI score. To further help guide in designing codon adapted sequences for use in this invention, 24044 RefSEQ database human transcript products have been analysed (NM_prefixed accession numbers) derived from NCBI genome build number 36. The CAI score range was calculated and was from 0.593 to 0.894 with an average score of 0.720. The highest score (0.894) for a known and expressed gene (rather than theoretical) in this database was generated by the keratin associated protein 5-8 (KRTAP5-8; NM_021046) and by the late cornified envelope 1A (LCE1A; NM_178348). Additionally a database of 21182 human IgG cDNA's revealed that IgG scores range from 0.576 to 0.878 with an average of 0.766. To help guide those skilled in the art, sequences suitable for use in the invention could possess CAI scores above and beyond that of naturally occurring highest human genes such as the late cornified envelope 1A (LCE1A; NM_178348). More preferably CAI scores above 0.9 should be employed.

It was observed that if codon adaptation was carried out across a shorter sequence (for example just the variable region) then an increased level of high producing clones is observed however, when codon adaptation is carried out across the entire open reading frame then the breadth (i.e. number) of high producing clones generated is increased still further (see Table 5).

Due to the sequence of preferred codons, typical adaptation approaches will normally by default also avoid introducing high-scoring ARE (AU Rich Elements see Akashi et al Blood 1994; Vol 83 pp 3182-3187)) RNA instability sequences. However occasionally after codon adaptation there is a requirement to remove expression disrupting sequence elements accidentally introduced. These include but are not limited to:

(i) Functioning splice sites,
(ii) Areas of dyad symmetry (e.g. direct, inverted or palindromic sequences) that noticeably reduce expression levels and/or increase recombination rates between the sequences.
(iii) Functioning instability sequences.

On the rare occasions when such unwanted disruptive elements are created during adaptation it is recommended a less preferred but not least preferred human codon (unless choice is limited) be employed to disrupt the local sequence to inactivate function. Small deviations from maximal scores will not significantly impact use of the resulting open reading frames in this invention.

It is also recognised that if small areas of an open reading frame remain non-adapted (e.g. to retain useful restriction sites) then this will not significantly impact overall CAI score.

If the open reading frame encodes for a fusion, hybrid or chimeric protein it is encouraged that the CAI score is increased in a same manner as described above. Again this adaptation towards synonymous codons preferred by the host cell for the expression of highly expressed endogenous genes should be undertaken for each and every component of gene or cognate cDNA of the fused or engineered open reading frames. For purely synthetic coding sequences present in a protein (i.e. sequence for which no prior sequence exists) it is advised to introduce unnaturally high human gene CAI scores in precisely the same manner. Open reading frames with CAI scores of above and beyond the late cornified envelope 1A human gene should be employed in this invention.

The present invention herein described is the first to describe a method of reducing the levels of a selectable and amplification agent required, the time required, and the number of amplification cycles required in order to generate genetically engineered cell lines expressing desired levels of protein by codon adaptation of the open-reading-frames encoding the protein. Through the use of codon adaptation for this purpose sufficient yields are being observed in faster time frames and so saving many weeks in cell line development activities. Furthermore we are also generating equivalent or improved cell lines by using lower concentrations of selection and amplification agent than we have ever previously achieved. Indeed it is likely that when such improvements as described herein are combined with standard cell culture and seeding protocol improvements as those described by Celina de la Cruz Edmonds et al (ibid), further reductions in the levels of selection and amplification agents, and further reduction in the time needed to generate equivalent or improved yields from genetically engineered cell lines, will be observed.

The present invention is suitable for use when the therapeutic protein is a glycoprotein. Whilst previous work discloses the fact that one can control protein product glycosylation by modification of process duration, temperature, pH, osmolarity and media constituents and additives etc (e.g. see WO2002076578 and references therein), we have found that codon adaptation of open reading frames encoding therapeutic polypeptide sequences (in the case of antibody therapeutic polypeptides) is able to decrease levels of incomplete glycosylation and levels of reduced site occupancy independently of CHO cell sub-type, selection and amplification regimes or media culture conditions.

This surprising observation is the first to demonstrate that one can impact protein glycosylation profile via open reading frame codon adaptation. By employing the codon-adaptation approaches as described herein, a robust manufacturing process can thus be ensured which depends on the sequence of the gene rather than the conditions that the host cell is grown in. In turn this allows for greater opportunity to improve culture conditions and feed regimes through traditional media and feed development iterations without excessive concern over the resulting impact on the product glycoprofile.

The degree of codon adaptation can be measured using the method first described by Sharp and Li (Nucleic Acid Res 1987 15:1281-95). Sharp and Li proposed the Codon Adaptation Index (CAI) score which is essentially derived from the codon preference statistics, but normalized for each amino acid so as to exclude the effects of variation in amino acid composition between different genes. This CAI metric is readily available (e.g. via EMBOSS The European Molecular Biology Open Software Suite (see Rice et al 2000: Trends in Genetics 16; pp 276-277)).

In order to score open reading frames intended for use in this invention, one must first use the appropriate reference database. First one should consider the cell host to be used then one should identify a reference table of relative synonymous codon usage (RSCU) for expressed genes in said cell host. Typically human RSCU databases are suitable for reference when expressing resulting open reading frame in any mammalian cell type. One example of a database is that provided by EMBOSS which uses as a reference the Ehum.cut codon usage table to determine codon usage preferences in human cells. An alternative reference codon usage table is that described by Massaer et al (ibid) in which a smaller number of highly expressed human genes are employed to determine codon preference. Whilst these two reference tables broadly agree on the most preferred codon, there is one notable divergence for one amino acid (arginine). Therefore when designing open reading frames for use in this invention it is logical to cross reference the same codon usage tables to (i) determine the most preferred codons to include in the open reading frame and then (ii) CAI score the open reading frame subsequently generated to ensure the score is sufficiently high to be suitable for use in this invention. For example if the Massaer et al database is employed regularly to design open reading frames for expression in human and mammalian cells and therefore CGC codon is considered most preferred to encode arginine then it is logical to also use this preference reference data when determining the CAI score of the resulting open reading frames generated.

The methodology as described herein is particularly suitable when expressing antibodies or derivatives thereof and is particularly effective when combined with expression cassettes driven by promoter and expression elements derived from the EF-1 alpha gene. Expression cassettes driven by other promoter and expression elements (e.g. derived from the RSV LTR) are also suitable. It is well known in the art that expression cassette elements (for example promoters, enhancers, matrix attachment regions (MARS), insulators, untranslated regions, intervening sequences such as introns and polyadenylations sites) can be combined in many different combinations to create suitable expression cassettes to drive expression of the desired open reading frames and to drive expression of the selection and amplification markers employed in this invention.

Once clones in any given cell line development protocol approach a production plateau in unfed extended batch production, it is observed that additional laboratory activities are best focused on methodologies such as (i) single cell cloning of the best clones, (ii) fed-batch process development, (iii) perfusion style process developments, (iv) bespoke media and feed recipes and regimes and (v) further culture adaptation. For example once a production threshold is reached for an individual clone, its derived single-cell sub-clones are normally more stable and high-yielding than amplified daughter clones generated by further selection and amplification regimes in yet more stringent levels of selection and amplification agent. Indeed increasing selection and amplification of final clones already approaching a threshold of production often leads to instability and after initial improvements, can often ultimately lead to similar or even lower titres in extended unfed production model batch cultures than the amplified parental clone. Therefore whilst it is recognised that on occasion a rare and fortuitous further amplification event may increase titres above 2-fold in some instances, once an expression threshold is approached, there are more reliable techniques that can instead be employed to increase stable titres still further.

The present invention is exemplified by and not limited by, the following examples.

EXAMPLES

In the past, DHFR selection methodology has been employed on more than fifteen antibody projects. In all cases when using this methodology at least two rounds of amplification and a minimum of 50 nM MTX as a selection and maintenance pressure to generate cell lines with suitable yields has been necessary. Typical results generated over this period of time by this methodology are represented by antibodies 1, 2, 3 and 4 in Table 1. Antibody project 1 was carried out using standard methodologies available at the time. Antibody projects 2-9 were carried out according to the materials and methods below.

The impact of improving the codon adaptation index (CAI) of open reading frames was studied.

Antibody 5 was first chosen for investigation. This study involved expressing the antibody product from wild-type (i.e. non codon-adapted) heavy and light chain antibody open reading frames (recorded as antibody 5 (a)), heavy and light chain open reading frames with codon adaptation broadly of the variable domain coding sequences only (recorded as antibody 5 (b) or 5 (c)) or codon adaptation of the entire heavy and light chain open reading frames (recorded as antibody 5 (d)). The results of this study are presented in Tables 1-5.

Example 1, Materials and Methods 1.1 DNA Cloning and Vector Construction.

All DNA cloning was performed by established restriction enzyme based sub-cloning and PCR assembly methodologies (see Molecular Cloning: A Laboratory Manual. Third Edition: Sambrook et al (CSH Laboratory Press)). Schematic representations of the expression and selection vectors are shown (see FIG. 1). Vectors shown exemplify the RSV promoter however, different promoters were used according to table 1. In all other respects the vectors remained unchanged.

1.2 Codon Adaptation.

In projects where CAI adapted ORF sequences were investigated, these were generated using desired overlapping oligonucleotides combined with the aid of standard fusion polymerase chain reaction (PCR) prior to cloning and sequence confirmation; all by standard methodology (see Molecular Cloning: A Laboratory Manual. Third Edition: Sambrook et al (CSH Laboratory Press) and Stemmer et al., Gene. 164(1):49-53, 1995). The sequences of the adapted regions of the ORFs of project 5 (b) and 5 (c) were designed using the Massaer Codon Usage preference for human/mammalian cells (see FIG. 11).

For antibody project 5 (d), the codon adapted ORF sequences were designed and generated by contract service provider 1. The resulting ORFs possessed a CAI score of >0.9. The codon adapted sequences encoding the antibody variable domains for antibody project 6 were designed and generated by contract service provider 2. These variable domains were then combined with the codon adapted constant domains encoding sequences of project 5 (d) by standard sub-cloning with aid of unique cloning sites located between constant and variable regions (using SpeI for heavy chain, BsiWI for light chain) (projects 6 (b) and 6 (d)). The resulting ORFs encoding the full length antibody for project 6 (b) and 6 (d) each possessed a CAI score of >0.9. The entire codon adapted ORFs of antibody project 7 were designed and made by contract service provider 2 and the resulting ORFs possessed a CAI score of >0.9. The ORFs of projects 8 and 9 employed the Leto software algorithm to design the variable domain sequence. In-frame full-length open-reading-frames were then generated by combining these sequences with appropriate constant domain encoding sequences (again using the SpeI and BsiWI sites as above): For antibody 8, the sequences encoding the variable domains were fused with the respective constant domain encoding sequences from project 7. For antibody 9, the variable domain encoding sequences generated were fused with the respective constant domain encoding sequences from project 6 (d). Once more the resulting ORFs encoding the entire heavy and light chains for project 8 and 9 each possessed CAI scores >0.9.

In FIG. 11(A). The light chain sequence encoding the CDR1 of antibody project 5 is shown as a representative sample sequence. The amino acid sequence of this CDR is shown. An example potential auuua instability AU rich element (ARE) is shown boxed and bold (see also Akashi et al Blood 83: pp 3182-3187). The arginine codon is also highlighted. First, the increased codon adaptation method resulted in an increased CAI score across the ORF. This antibody was employed in project 5 (b). As shown this method included most preferred codons (e.g. for Tyr) but not on all occasions (e.g. Leu). Second, the maximal CAI score employed the most preferred codons according to Massaer et al. This sequence was employed in antibody project 5 (c). The final sequence provided, employed the most preferred codons according to a larger database such as that available on the Codon Usage Database website. This antibody sequence was employed in project 5 (d). In FIG. 11(B) The codon preference tables of highly expressed genes in humans adapted from Massaer et al. In FIG. 11(C) The codon preference table for human genes adapted from The Codon Usage Database (www.kazusa.org.jp/codon) for *Homo sapiens* (comprising 89533 CD's (38691091 codons).

Note for both heavy and light chain ORFs, unique Hind III (5') and EcoR1 sites (3') were routinely employed to shuttle open reading frames into the expression vectors.

All sequences were confirmed prior to use in transfection.

For example sequences see FIGS. 2, 3, 4, 5, 6, 7, 8 and 9 which record the original and adapted open reading frame sequences of project 5. Note that in project 5 only 5 (d) was sufficiently codon adapted on regions of the open reading frames for the resulting CAI score to go above 0.9.

For all CAI scores reported herein, the Ehum.cut codon usage table was used for reference (available via EMBOSS).

These scores are calculated using the Codon Adaptation Index application which employs the methodology first described by Sharp and Li (ibid). This application is part of the EMBOSS suite. Version 2.8.0 Ehum.cut codon usage files and the default parameter settings were used to determine the CAI scores of the sequences.

TABLE 6

Ehum.cut codon usage table derived from EMBOSS. Column A: Codon sequence; Column B: amino acid encoded; Column C: Proportion of usage of a given codon among its redundant set; Column D: Number of codons per 1000 codons; Column E: Number of times codon observed in data set used to derive the table.

| (A) | (B) | (C) | (D) | (E) |
| --- | --- | --- | --- | --- |
| GCG | A | 0.100 | 6.950 | 10994 |
| GCA | A | 0.220 | 15.370 | 24296 |
| GCT | A | 0.270 | 18.750 | 29645 |
| GCC | A | 0.410 | 28.340 | 44818 |
| TGT | C | 0.440 | 9.970 | 15764 |
| TGC | C | 0.560 | 12.630 | 19971 |
| GAT | D | 0.460 | 22.530 | 35629 |
| GAC | D | 0.540 | 26.940 | 42601 |
| GAA | E | 0.420 | 29.040 | 45923 |
| GAG | E | 0.580 | 40.670 | 64302 |
| TTT | F | 0.450 | 16.640 | 26304 |
| TTC | F | 0.550 | 20.620 | 32611 |
| GGT | G | 0.170 | 11.880 | 18792 |
| GGG | G | 0.240 | 16.520 | 26128 |
| GGA | G | 0.250 | 17.710 | 28000 |
| GGC | G | 0.340 | 23.940 | 37852 |
| CAT | H | 0.400 | 9.660 | 15276 |
| CAC | H | 0.600 | 14.350 | 22687 |
| ATA | I | 0.150 | 6.920 | 10941 |
| ATT | I | 0.350 | 16.280 | 25738 |
| ATC | I | 0.500 | 23.380 | 36976 |
| AAA | K | 0.410 | 24.120 | 38145 |
| AAG | K | 0.590 | 34.370 | 54344 |
| CTA | L | 0.070 | 6.320 | 9990 |
| TTA | L | 0.070 | 6.400 | 10123 |
| TTG | L | 0.120 | 11.520 | 18218 |
| CTT | L | 0.130 | 11.740 | 18564 |
| CTC | L | 0.200 | 18.690 | 29552 |
| CTG | L | 0.420 | 38.790 | 61342 |
| ATG | M | 1.000 | 22.230 | 35143 |
| AAT | N | 0.450 | 17.340 | 27422 |
| AAC | N | 0.550 | 21.190 | 33512 |
| CCG | P | 0.110 | 6.700 | 10588 |
| CCA | P | 0.280 | 16.810 | 26574 |
| CCT | P | 0.280 | 16.970 | 26837 |
| CCC | P | 0.330 | 19.900 | 31463 |
| CAA | Q | 0.260 | 11.930 | 18863 |
| CAG | Q | 0.740 | 33.220 | 52535 |
| CGT | R | 0.090 | 4.770 | 7535 |
| CGA | R | 0.110 | 6.040 | 9547 |
| CGC | R | 0.200 | 10.750 | 17002 |
| AGG | R | 0.200 | 10.780 | 17049 |
| AGA | R | 0.200 | 10.820 | 17104 |
| CGG | R | 0.200 | 10.830 | 17126 |
| TCG | S | 0.060 | 4.390 | 6942 |
| TCA | S | 0.140 | 11.070 | 17497 |
| AGT | S | 0.150 | 11.180 | 17681 |
| TCT | S | 0.180 | 14.120 | 22320 |
| TCC | S | 0.230 | 17.320 | 27389 |
| AGC | S | 0.250 | 18.890 | 29874 |
| ACG | T | 0.120 | 6.550 | 10364 |
| ACT | T | 0.240 | 13.250 | 20954 |
| ACA | T | 0.270 | 15.220 | 24071 |
| ACC | T | 0.370 | 20.980 | 33176 |
| GTA | V | 0.110 | 6.920 | 10939 |
| GTT | V | 0.170 | 10.880 | 17196 |
| GTC | V | 0.250 | 15.440 | 24415 |
| GTG | V | 0.470 | 29.080 | 45989 |

TABLE 6-continued

Ehum.cut codon usage table derived from EMBOSS. Column A: Codon sequence; Column B: amino acid encoded; Column C: Proportion of usage of a given codon among its redundant set; Column D: Number of codons per 1000 codons; Column E: Number of times codon observed in data set used to derive the table.

| (A) | (B) | (C) | (D) | (E) |
|-----|-----|-------|--------|-------|
| TGG | W | 1.000 | 12.430 | 19658 |
| TAT | Y | 0.430 | 12.320 | 19479 |
| TAC | Y | 0.570 | 16.510 | 26110 |

1.3 Cell Culture.

Suspension-adapted CHO DG44 cells were routinely passaged in animal-derived-component-free-media to which they had been previously adapted. This media consisted of a basal formulation containing amino acids, trace elements, vitamins, glucose, and yeast hydrolysate. This media was also supplemented with recombinant insulin, lipids and nucleosides. Sodium bicarbonate was added to media as a buffer. Many equivalent animal derived component free media recipes are known in the art. Initial selection for vector transformed cells was undertaken by nucleoside withdrawal (for DHFR selection) and G418 addition (for neomycin phosphotransferase selection). For titre ranking, the 96-well assay titres were prone to variation induced by cell growth, seeding numbers, media dispensing volumes, and evaporation kinetics across a plate. As a consequence the titres generated in shake flasks production models were more indicative of cell line rank order in high-yielding, amplified cell lines. For such models all cells were seeded at the same initial density. In such models, viability and growth were also monitored.

1.4 DNA Preparation Before Transfection

Equal amounts (15 µg) of the heavy-chain and light-chain expression vector were linearised to completion (with Not I) in a 200 µl volume eppendorf reaction and then ethanol/sodium acetate precipitated. The pellet was then washed in 70% ethanol, air dried and re-suspended in 50 µl of molecular-biology grade water.

1.5 Preparation of CHO DG44 Cells Before Transfection $1.2 \times 10^7$ cells (per transfection) of healthy growing cells were spun (1000 rpm for 2-10 minutes) in a 15 or 50 ml tube, washed in 15 ml of ice-cold PBS/sucrose, spun again and then re-suspended in 800 µl of ice-cold PBS sucrose. This cell suspension was then added to the previously prepared DNA and left on ice for 15-minutes before being transferred to a chilled electroporation cuvette.

1.6 Electroporation

The cuvette containing the prepared DNA and cells was electroporated in a Gene Pulser set to 25 µF and 0.38 kV and then returned to ice for 10 minutes. The cells were then removed and added to 240-mls of non-selective media and then plated in non-selective media in 40×96-well dish at $2-5 \times 10^3$ cells per well (i.e. 50 µL per well). The plates were then wrapped in foil and incubated at 37° C. and 5% $CO_2$ for 48 h.

1.7 Selection, Amplification and Clone Identification 48-hours after electroporation, 150 µL of selective media was added to each well. This selective media contains G418 and no nucleosides. Once a week thereafter, 140 µl of media was carefully exchanged for fresh selective media without disturbing the settled cell layer and after 3-4 weeks, all growing clones (typically growth of 0.1 colony per well; i.e. growth in 10 wells per 96-well plate) were titred for antibody production. The top ranking clones (typically 20-100) identified were then scaled-up in the same selective media through 24-well dishes and up to 6-well dishes. These clones were then plated at 1000 cells/per well in a 96-well dish (96-wells per clone) and then selected on selective media also containing 5 nM methotrexate in a volume of 200 µl per well. After additional two to three weeks incubation, the best clones were again scaled up and then re-plated at 1000 cells per well but in 50 nM MTX. These clones were also screened in 96-well plates after 2-3 weeks of growth and the best scaled up and then plated at 1000 cells per well in 96-well dishes but with 150 nM MTX. In order to evaluate final clones for production potential, the best clones at 150 nM MTX were then scaled-up and evaluated in shake flask production models for titre and quality of the product generated. The best clone for project 5 (a) was a clone labelled 17-9-6-1. This generated 0.3 g per litre end-titre in unfed production models.

NB. Levels of methotrexate and the number of rounds of amplification required in step 1.7 varied depending on the project and whether the sequences were codon adapted.

1.8 Titre Analysis.

For media samples obtained from 96-well plates, antibody titre was determined by automated 96-well sandwich ELISA style methodology on an IGEN M-Series M8/384 analyser (Bioveris, MaryLand, USA) with manufacturer's recommendations and standard methodologies. The sandwich consisted of Streptavidin coated magnetic coated beads, Biotinylated-Protein A and Ruthenium labelled F(ab)2 fragments. The signal generated for the test sample was then compared to a serial dilution of the antibody reference standard. Whilst a highly sensitive assay, due to assay variation combined with cell growth variables at 96-well cultures, assay intermediate precision and reproducibility is relatively low for this assay for high-yielding, amplified cell lines. For media samples obtained during shake flask and bioreactor production modelling, antibody titre was measured with the aid of a nephelometric method where a light signal is scattered by the insoluble immune-precipitin in the reaction solution using a Beckman Coulter Image system (Buckinghamshire, England) and manufacturer's recommendations and standard methodologies. The signal generated for the test sample again being compared to a serial dilution of the antibody reference standard. All titres reported are approximate.

1.9 Bioreactor Shake Flask Models (Extended Unfed Batch Production Models).

Typically cells were seeded in standard 250 ml tissue-culture shake-flasks at 800,000 cells per ml with vented lids containing animal-derived-component-free media and to total volume of 120 mls. These flasks were then incubated with agitation in carbon dioxide enriched air and set temperatures to encourage and sustain cell growth. Various conditions were tested for each clone—for example at various temperature conditions. In the results reported herein the highest titre for each clone (across standard conditions) tested is exemplified. Typically the production model end point titres as reported herein were recorded at the point at which cell viability drops to approximately 50% as determined by trypan blue exclusion based assay on a Vi-Cell (Beckman) using standard Vi-Cell CHO parameter settings and manufacturer's recommended protocol. Typically this end-point titre is generated after 10-20 days incubation.

1.10 Bioreactor Culture Methodology.

Standard bioreactor culturing methodologies and equipment were employed at all times. Typically to generate a seed train, cells were scaled up into larger volumes and passaged twice a week on a repeated 3-day then 4-day regime. For the work shown in FIG. 13, seed cells were then used to inoculate 3-litre Applikon bench top bioreactors (2-litre working volume) run under the following process conditions: Temperature $34^2$C, pH set point 6.95, DO set point 30%. As with Shake flask models, cultures were extended until cell viability dropped to approximately 50%. These bioreactors broadly mimic end-point titre of both shake-flask as well as larger bioreactors used to supply clinical trial material etc.

1.11 RT-QPCR Analysis (for Results, See FIG. 10).

CHO RNA extractions and RT-QPCR reactions were undertaken by automated silica based extraction using the MagNA Pure and the RNA High Performance RNA Isolation kit and protocols (Roche). Following reverse transcription using random hexamers, the PCR reaction was undertaken using an ABI-7700 (Applied Biosystems) and analysed via the ΔΔCt relative quantitation algorithm using standard methodology. The reactions were multiplexed (18S+ Target gene [heavy chain/light chain]), 18S being the most abundant target was primer limited to prevent inhibition of the target reactions. Probes and flanking primer pairs employed for Q-PCR were used according to SEQ ID. NO's 1-9

Note that the heavy chain and light chain probes/primers above were not suitable for use with project 5 (d) due to increased ORF codon adaptation undertaken in this project hence their exclusion from FIG. 10 (A).

1.12 Western Blot Analysis (for Results See FIG. 10).

Standard methodology was employed and is described in detail elsewhere (e.g. see Sambrook et al IBID). In brief polyclonal equivalent cell extracts were made using whole cell lysis and protein extraction buffer. Equal amounts of each extract were then heat incubated with Laemmli loading buffer and then loaded and run on SDS-Page gels with tris-glycine running buffer to separate the protein fractions. Once separated, the proteins were then electro transfer blotted onto nitrocellulose membranes and then probed with a whole anti-human IgG (HRP conjugated). A signal was generated by incubation with an HRP substrate and recorded with X-ray film. An additional longer exposure was required to detect antibody light-chain product for project 5 (a).

1.13 Fluorescent Methotrexate Staining to Determine DHFR Levels in Clones Producing Desired Recombinant Protein.

Each clone was cultured without methotrexate for 4-5 days prior to addition of 10 μM Alexa-Fluor 488—Methotrexate (Molecular Probes/Invitrogen, Paisley) for 18-22 hrs at 37° C. 5% $CO_2$ to 700,000 live cells. Stained cells were then harvested and washed with media and incubated at 37° C., 5% $CO_2$ for 30 mins. Harvested cells were washed again with media and then re-suspended in media, filtered and live/dead exclusion dye Propidium Iodide (Sigma, St Louis) was added before analyzing on BD FACS ARIA. Data shown in FIG. 14 (A) are of gated live cells only.

1.14 qPCR Analysis of Genomic DNA for DHFR and Neo Levels.

CHO genomic DNA extraction was performed using standard kits from Qiagen. Following DNA quantitation and normalisation using a spectrophotometer reading, the PCR reaction was undertaken using an ABI-7700 (Applied Biosystems) and analysed via the ΔCt relative quantitation algorithm using standard methodology. Probes and flanking primer pairs employed for Q-PCR were used according to SEQ ID. No's 20-25. results are shown in FIG. 14 (B).

Example 2, Expression of Monoclonal Antibody Heavy and Light Chains in CHO Cells Surprisingly whilst the high CAI scoring ORF's, but still of natural score (i.e scoring less than highest observed natural human ORF's such as late-cornified envelope a! LCE1A; NM 1783480) of project 5 (c) generated a higher top titre than the unnaturally high CAI scoring open reading frames of project 5 (d), the breadth (number) of high producers in 5 (d) were improved (see Table 5). The best clones of 5 (a), (c) and (d) were then amplified and evaluated further. For this further evaluation, the 5 (a) clones were progressed as the control and to represent the typical project titres observed prior to the results described herein. The results of this work generated a high producing, stable clone (titre and growth observed for 40 passages) from project 5 (d) in an unexpectedly fast time and with reduced levels of amplification. Indeed the levels of methotrexate required to generate the final cell line from 5 (d) was significantly lower (97% less methotrexate) relative to that required to generate equivalent cell lines expressing similar or lower levels of the same protein product from non codon-adapted open-reading-frames of project 5 (a) (see Table 1). Further detailed analysis was carried out—See Tables 2-4.

To investigate if the binding properties of the resulting recombinant proteins generated by modified CAI scored ORFs were impacted by codon adaptation, the binding characteristics were compared and analysed for the antibody of project 5 encoded by either ORFs of CAI score 0.809 (HC)/0.761 (LC) or by ORFs of CAI score 0.982 (HC)/0.976 (LC). Both materials were generated in bioreactors and then purified by equivalent purification regimes. Through this comparison it was shown that the binding characteristics of the antibody were unaffected by the CAI alterations to the ORFs that encoded this antibody.

From project 5 (d) the top producing clone, 097-7, as shown in Table 1, was single-cell cloned to ensure clonality of the cell line, with the resulting titre of the best sub-clone generating a near 2-fold increase in unfed extended batch cultures relative to the non-cloned parent. The titres shown in FIG. 13 are generated from unfed batch cultures in two separate 3-litre Applikon bench top bioreactors as described in 1.10.

TABLE 1

For each protect, the final clone chosen for subsequent further development and banking is presented. Also highlighted are the 96-well titres (ng/ml) generated for each final clone at each stage of its cell line development. Typical data generated prior to the results as described herein are represented as antibody projects 1, 2, 3 and 4. Note that project 2 and project 4 express the same product. For project 2 and 4 all activities were carried out in two independent laboratories using the same vectors, host cells and protocols but different lab operators and equipment. All titres shown below at the 0, 5, 50 and 150 nM MTX are those generated at 96-well stage. Higher titrations showed no significant improvement in batch production models and so lower MTX clone progressed (see Table 2). FIO = For information only, not required. Project 6 (a) was discontinued before plateau was reached due to better titres from projects 6 (b) -6 (d).

| | Antibody | | | | | | |
|---|---|---|---|---|---|---|---|
| | 1 | 2 | 3 | 4 | 5 (a) | 5 (d) | 6 (a) |
| Final Best Clone | ACC522(L4) | 15-27-4 | C9-13-9 | 129-1-3-1 (DRC349) | 17-9-6-1 | O97-7 | 141-6-4 (best A2 96-well titre) |
| 0 nM MTX | 120 | 110 | 20 | 41 | 12 | 340 | 16 |
| 5 nM MTX | 530 | 180 | 150 | 920 | 32 | 880 | 72 |
| 50 nM MTX | 1720 | 1240 | 490 | 5231 | 310 | 6700 (FIO) | 438 |
| 150 nM MTX | Not Required | Not Required | 1910 | 23000 | 1670 | Not Required | Not undertaken-required |
| Codon Optimised? | No | No | No | No | No | Yes | No |
| Promoter | CMV | RSV | RSV | RSV | RSV | RSV | RSV |
| CAI (Heavy Chain) | 0.679 | 0.811 | 0.814 | 0.811 | 0.809 | 0.982 | 0.818 |
| CAI (Light Chain) | 0.674 | 0.767 | 0.763 | 0.767 | 0.761 | 0.976 | 0.755 |
| Weeks to generate final line in 96 well | ~15 | 12 | 19.5 | 18 | 19 | 7 | >15 |
| Non-Fed Production Bioreactor Model (% MTX) | 0.3 g (100%) | 0.3 g (100%) | 0.5 g (300%) | 0.9 g (300%) | 0.2 g (300%) | 0.7 g (10%) | Not determined- estimated at <0.1 g (100%) |

| | Antibody | | | | | | |
|---|---|---|---|---|---|---|---|
| | 6 (b) | 6 (c) | 6 (d) | 7 (a) | 7(b) | 8 | 9 |
| Final Best Clone | 280-9-6 | 58-3-3 | P100-1 | C65-5 | 74-3 | 454-6 | 390-8 |
| 0 nM MTX | 78 | 76 | 2350 | 64 | 2054 | 1280 | 2055 |
| 5 nM MTX | 1140 | 1160 | 2025 | 5700 | 2125 | 1690 | 14055 |
| 50 nM MTX | 4170 | 5775 | Not Required | Not Required | Not Required | Not Required | Not Required |
| 150 nM MTX | Not Required | Not Required | Not Required | Not Required | Not Required | Not Required | Not Required |
| Codon Optimised? | Yes | No | Yes | Yes | Yes | Yes | Yes |
| Promoter | RSV | EF-1a | EF-1a | RSV | EF-1a | EF-1a | Ef-1A |
| CAI (Heavy Chain) | 0.976 | 0.818 | 0.976 | 0.977 | 0.977 | 0.954 | 0.975 |
| CAI (Light Chain) | 0.978 | 0.755 | 0.978 | 0.973 | 0.973 | 0.919 | 0.973 |
| Weeks to generate final line in 96 well | 14 | ~15 | 10 | 8.5 | 8.5 | 7.5 | 8 |
| Non-Fed Production Bioreactor Model (% MTX) | 0.5 g (100%) | 0.9 g (100%) | 0.9 g (10%) | 0.4 g (10%) | 0.5 g (10%) | 0.6 g (10%) | 2.2 g (10%) |

TABLE 5

Titre comparison of non-amplified clones generated by standard transfection and selection protocol and then selected on nucleoside withdrawal and G418 addition. All cell lines contain the same vectors expressing the same antibody (of project 5) but from open reading frames encoding with differing CAI scores. For project 5 (a) (non-optimised) three further transfections were performed but are not shown as results were essentially background. In Figure (A) "% titre > 5 ng" refers to the % of wells after screening recording above 5 ng/ml. "% titre > 50 ng/ml" refers to the % of wellsscreened recording above 50 ng/ml. "Top titre" refers to the highest scoring titre of all screened. "$50^{th}$ Value" refers to the $50^{th}$ best titre screened. "$20^{th}$ value" refers to the $20^{th}$ best titre screened. In (B), the average results for Top, $20^{th}$ and $50^{th}$ titres reported in (A) are represented in histogram format.

| Transfection | HC CAI SCORE | LC CAI SCORE | % with titre > 5 ng/ml | % with titre > 50 ng/ml | Top titre | $50^{th}$ value | $20^{th}$ value |
|---|---|---|---|---|---|---|---|
| 1 | 0.809 | 0.761 | 23 | 0 | 43 | 6 | 8 |
| 2 | 0.809 | 0.761 | 26 | 0 | 16 | 5 | 6 |
| 3 | 0.809 | 0.761 | 26 | 0 | 23 | 6 | 7 |
| 4 | 0.847 | 0.833 | 43 | 7 | 376 | 2 | 17 |
| 5 | 0.847 | 0.833 | 62 | 24 | 778 | 9 | 76 |
| 6 | 0.872 | 0.894 | 47 | 20 | 674 | 23 | 105 |
| 7 | 0.872 | 0.894 | 63 | 30 | 923 | 12 | 103 |
| 8 | 0.982 | 0.976 | 57 | 25 | 706 | 46 | 178 |
| 9 | 0.982 | 0.976 | 82 | 61 | 653 | 80 | 171 |

TABLE 3

Detailed titre analysis in 96-well plates of the projects shown in Table 1. Titre of the best and the $50^{th}$ best clone is shown after G418 addition and nucleoside withdrawal selection but with no methotrexate addition.

| Project | Codon Adaptation? | Promoter used to drive expression of antibody ORFs | Top Titre (ng/ml) | 50th Titre (ng/ml) |
|---|---|---|---|---|
| 2 | No | RSV | 130 | 2 (22nd) |
| 3 | No | RSV | 71 | 12 |
| 4 | No | RSV | 152 | 22 |
| 5 (a) | No | RSV | 43 | 6 |
| 5 (d) | Yes | RSV | 653 | 80 |
| 6 (a) | No | RSV | 116 | 14 |
| 6 (b) | Yes | RSV | 840 | 89 |
| 6 (c) | No | EF-1a | 1153 | 87 |
| 6 (d) | Yes | EF-1a | 2499 | 1426 |
| 7 (a) | Yes | RSV | 830 | 50 |
| 7 (b) | Yes | EF-1a | 3467 | 528 |
| 8 | Yes | EF-1a | 4090 | 739 |
| 9 | Yes | EF-1a | 3108 | 573 |

TABLE 4

The top 20-100 clones as observed in projects 5 and 6 were then scaled into 6-well dishes before being re-plated into 96-wells in media containing 5 nM methotrexate. The mean and high titres of growing clones observed in experiments 5 and 6 selected at 5 nM (A1) and 50 nM (A2) concentrations of the methotrexate antifolate in 96-well dishes are shown below.

| | A1 5 nm MTX | | A2 50 nm MTX | |
|---|---|---|---|---|
| Project | Mean Titre | Max Titre | Mean Titre | Max Titre |
| 5 (a) | 42 | 253 | 137 | 452 |
| 5 (d) | 626 | 1760 | 1130 | 9500 |
| 6 (a) | 134 | 316 | 129 | 809 |
| 6 (b) | 761 | 6340 | 2525 | 15030 |
| 6 (c) | 593 | 2592 | 949 | 3884 |
| 6 (d) | 1012 | 5075 | 3017 | 12360 |

TABLE 2

Examples of production plateaus: Example (A) the final chosen clone for Project 5 (d) was amplified further in 50 nM MTX. The unfed production models titres of parent clone (shaded) and resulting highest titre of 'amplified' daughter clones are shown. Similar examples (B, C, D, E, F, G) also shown. For each example the highest titre of daughter clone after further amplification is recorded. This demonstrates that reaching higher titres earlier is more beneficial than attempting to reach higher titres through further rounds of amplification.

| Example | Cell Line | MTX levels | 96-well titres (ng/ml) | Production Model end-point titres (mg/l) | % change in production model end-point titre after further amplification |
|---|---|---|---|---|---|
| Example A: Chosen Clone Project 5 (d) | 097-7 | 5 nM | 880 | 690 | |
| | 097-7-1 | 50 nM | 6700 | 550 | −20% |
| | 097-7-3 | 50 nM | 3300 | 216 | −69% |
| | 097-7-5 | 50 nM | 3100 | 615 | −11% |
| | 097-7-6 | 50 nM | 1900 | 566 | −18% |

TABLE 2-continued

Examples of production plateaus: Example (A) the final chosen clone for Project 5 (d) was amplified further in 50 nM MTX. The unfed production models titres of parent clone (shaded) and resulting highest titre of 'amplified' daughter clones are shown. Similar examples (B, C, D, E, F, G) also shown. For each example the highest titre of daughter clone after further amplification is recorded. This demonstrates that reaching higher titres earlier is more beneficial than attempting to reach higher titres through further rounds of amplification.

| Example | Cell Line | MTX levels | 96-well titres (ng/ml) | Production Model end-point titres (mg/l) | % change in production model end-point titre after further amplification |
|---|---|---|---|---|---|
| Example B: Chosen Clone Project 6 (d) | P100-1 | 5 nM | 2025 | 901 | |
| | P100-1-8 | 50 nM | 4570 | 499 | −45% |
| Example C: Non-chosen clone Project 6 (d) | P100-6 | 5 nM | 1435 | 468 | |
| | P100-6-8 | 50 nM | 5650 | 125 | −73% |
| Example D: Non-chosen clone Project 6 (d) | P634-2 | 5 nM | 3205 | 692 | |
| | P634-2-4 | 50 nM | 3685 | 369 | −47% |
| Example E: Non-chosen clone Project 6 (d) | P502-1 | 5 nM | 2385 | 357 | |
| | P502-1-4 | 50 nM | 5325 | 157 | −56% |
| Example F: Chosen Clone Project 7 (a) | C65-5 | 5 nM | 5700 | 400 | |
| | C65-5-7 | 50 nM | 4515 | 168 | −58% |
| Example G: Chosen Clone Project 7 (b) | 74-3 | 5 nM | 2125 | 488 | |
| | 74-3-3 | 50 nM | 820 | 239 | −51% |

Example 3, Antibodies 6 and 7 and EF-1a Promoter

Codon-adaptation of the open reading frames of both the heavy and light chains for antibody 6 was carried out, again to generate final CAI scores across the ORFs of >0.9. (See Table 1). The wild-type/starting and codon-adapted open reading frames were expressed in RSV based promoter expression vectors as well as a human elongation-factor-1 alpha (EF-1a) promoter based expression vector in which cis acting insulator, enhancer and promoter expression elements are instead supplied from a non-viral promoter source. The results of this work again demonstrated that significantly less methotrexate was required to generate a final high producing cell line when the open reading frame of the desired protein were first codon-adapted. Indeed, transfection 6 (a) in which antibody 6 was encoded by non-adapted ORFs (ie. with CAI score of <0.9) was abandoned at 5 nM MTX stage prior to the generation of cells nearing a plateau of production. The amplification regime was not pursued further in transfection 6 (a) because it was evident that significant more resource and time would have been required to generate cell lines capable of producing equivalent yields of protein relative the yields already obtained from cell lines in which ORFs of >0.9 had been employed (ie transfections 6 (b) and 6 (d). Furthermore, when comparing like-for-like vectors plus or minus codon adaptation, it was observed that codon-adaptation always reduced antifolate levels required. Again, for project 7, codon adaptation was carried out in a similar manner to project 6 (see Table 1) and the codon adapted ORFs (CAI>0.9) were expressed in an RSV as well as in an EF-1a promoter based expression vector. Once again, and irrespective of promoter, equivalent high yielding cell lines were generated in a faster time and with less methotrexate from CAI adapted ORFs when compared to all previous projects in which non-adapted ORFs were employed to encode the recombinant products (summarised in Table 1).

Example 4, mRNA Levels

To further investigate this methodology the impact of codon adaptation on the levels of mRNA generated was investigated in like-for-like polyclonal cell populations expressing the same product (the antibody of project 5) from the same vectors but from open reading frames reporting differing CAI scores.

CHO Cells were co-transfected with heavy chain (HC) and light chain (LC) encoding expression vectors encoding the same protein product (antibody of project 5). Each transfected population was maintained as polyclonal pools. Each vector pair encodes the same antibody heavy chain (HC) and light chain (LC) but from open reading frames with differing CAI scores.

The results of this experiment are captured in FIG. 10 and reveal that a significant fold increase in mRNA levels is observed when the CAI score is raised for both heavy and light chain message relative to the non-adapted controls. An equivalent increase in RNA levels (relative to starting non adapted sequence) occurred in all adapted sequences analysed. Similarly, and within the limits of the western blot assay, an equivalent increase in intracellular protein levels was observed for all adapted sequences. However whilst such equivalence was observed in intracellular protein levels, there were difference in the levels secreted. It was observed that cells containing the unnaturally high CAI scoring open reading frames generated higher polyclonal titres. This further supports the finding that the breadth of high producing clones is improved when unnaturally high CAI scoring open reading frames are employed in cell line development protocols.

FIG. 10

(A): Intracellular RNA levels of HC and LC message measured by RT Q-PCR: All signals normalised to ribosomal RNA and fold increases are relative to signals generated for starting HC and LC vectors encoded by the non-codon adapted open reading frames. Y-axis: Values range from 0 to 50-fold increase in RNA signal. X axis: a (h) denotes negative control HC signal generated from RNA extracts taken from non-transfected cells (in duplicate); b (h) denotes HC signal generated from RNA extracts derived from cells transfected with non-codon adapted HC and LC expression vectors, as used for project 5 (a) (CAI scores of 0.809 for HC and 0.761 for LC); c (h) denotes HC signal generated from RNA extracts derived from cells transfected with codon adapted HC and LC expression vectors, as used for project 5 (b) (CAI scores of 0.847 for HC and 0.833 for LC); d (h) denotes HC signal generated from RNA extracts derived from cells transfected with further codon adapted HC and LC expression vectors, as used for project 5 (c) (CAI scores of 0.872 for the HC and 0.894 for the LC). Light chain signals generated from the same RNA extracts as described above are shown as a(l), b(l), c(l) and d(l) respectively.

(B): Western Blot Analysis; Equivalent cell extracts were separated by SDS-Page, blotted and interrogated with anti-product antibodies (HRP conjugated). Control of non-transfected cells is shown in lane 1. Polyclonal cells expressing product heavy and light chain open reading frames as follows; Lane 2 and 3; HC with 0.809 CAI score and LC with 0.761 CAI score (protein expressed from experiment b(h) and b(l) above, vectors equivalent as those used in project 5 (a); Lane 4 and 5; HC with 0.847 CAI score and LC with 0.833 CAI score (protein expressed from experiment c (h) and c (l) above, vectors equivalent as those used in project 5 (b); Lanes 6 and 7; HC with 0.872 CAI score and LC with 0.894 CAI score (protein expressed from experiment d (h) and d (l) above, vectors equivalent as those used in project 5 (c); Lanes 8 and 9; HC with 0.982 CAI score and LC with 0.976 CAI score (protein expressed by vectors equivalent as those used in project 5 (d).

(C); 24-hour product titres reported in ng/ml for polyclonal cells described in FIG. 10 (B).

Example 5, Different Methods to Achieve High CAI. Example (a) Project 8 and Example (b) Project 9 a) For project 8 the Leto software was used to design the variable domains. These were then fused to the identical constant domains previously generated for project 7 with aid of standard restriction enzyme digest and ligation methodology. The resulting heavy chain and light chain ORFs scored 0.954 and 0.919 respectively. These were then employed in a cell line development project and once again we generated high yielding cell lines in a faster time frame and with less methotrexate than ever previously employed prior to codon adaptation (see Table 1).

b) For project 9 again the Leto software was used to design the variable domains. These were then fused to the identical constant domains previously generated for project 6 (d) with aid of standard restriction enzyme digest and ligation methodology. The resulting heavy chain and light chain ORFs scored 0.975 and 0.973 respectively. These were then employed in a cell line development project and once again we generated high yielding cell lines in a faster time frame and with less methotrexate than ever previously employed prior to codon adaptation (see Table 1).

Example 6—Impact Upon Glycosylation

It was noted that the levels of non-glycosylated heavy chain (NGHC) were significantly lower when expressed from codon-adapted open reading frames relative to levels generated when expressed from non-adapted open reading frames even though the same host, culture media and DHFR selection and amplification system were employed for the expression in both situations. Even more interestingly similar high levels of NGHC were also observed when the same non-adapted open reading frames were instead expressed in different host cells employing in different culture conditions and different vector, selection and amplification regime (Glutamine Synthetase/MSX) (see FIG. 12). This correlation between codon-adaptation of the open reading frame and reduced levels of non-glycosylated heavy chain reveals that through increasing the CAI score of an open reading frame one can also improve the overall quality of the product.

6.1 Cell Line Development with the Lonza CHOK1SV and Glutamine Synthetase Selection System (FIG. 12).

Vector construction and cell line development were undertaken according to the recommended Lonza (Slough) protocols. The media employed at all times was CD-CHO (Invitrogen). Open reading frames employed in antibody project 5 (a) containing non-adapted open reading frames were first sub-cloned into the Lonza vectors pEE14.4 (for the light chain) and pEE6.4 (for the heavy chain). These vectors were then combined according to the recommended Lonza protocol into a single double gene vector expressing heavy and light chains. This vector was then delivered to the Lonza suspension adapted CHOK1 strain named CHOK1SV host cells using electroporation as per Lonza recommended instructions and selected and amplified with glutamine withdrawal and with the addition of MSX also as recommended. The resulting clones were titred at 96-well and the best scaled-up into shake flasks and further evaluated. The best clone was selected to make product in large-scale bioreactors. For further general details on this approach see de La Cruz Edmonds et al 2006 Molecular Biotechnology 34:179-190)

6.2 Product NGHC Analyses

Protein was purified from culture supernatant with aid of protein A columns. The product was subsequently analysed with SDS capillary electrophoresis lab-on-a-chip equipment (Agilent Technologies, Cheshire UK) under reducing conditions and according to manufacturer's protocol. The non-glycosylated heavy chain is observed as a slightly faster migrating species relative to the main glycosylated heavy chain species (See FIG. 12B).

FIG. 12—Table (A) showing representative data from all analyses. Also included is additional work undertaken to express the non-adapted open reading frames in a different selection and amplification protocol (Glutamine synthetase/methotrexate) employing a different host cell, vector, media and culture regime (See example 6.1 above). (B) Example NGHC traces observed from starting non adapted ORFs versus codon-adapted ORFs. This analysis was undertaken on product purified from equivalent sized (1000-litre) bioreactors. In these representative trace overlays, harvest of bioreactors cell cultures expressing product from non-adapted ORFs (CAI: HC 0.809, LC 0.761) generated heavy chain with reduced site occupancy (10% non-glycosylated heavy chain) relative to product produced from adapted ORFs (CAI: HC 0.982, LC 0.976) which contained only 1.5% non-glycosylated heavy chain.

Example 7 Impact on Levels of Selection and Amplification Agents in the Final Cell Lines The addition or stepwise titration of increasing amounts of the MTX selection and amplification agent in the DHFR selection system is undertaken in order to augment expression by increasing gene copy number. To investigate the impact of codon adaptation on the gene copy number of the transfected plasmid DNA, two different semi-quantitative methodologies were employed (see sections 1.13 and 1.14 for the description of the experiments).

Firstly FACS analysis was used. For this purpose the final cell lines or single cell clones thereof for projects 2, 3, 4, 5 (d), 6 (d) and 7 (b) were stained with fluorescent methotrexate and analysed by FACS. The results (shown in FIG. 14A) demonstrate that the levels of methotrexate, as indicated by the mean fluorescence intensity, and therefore the levels of DHFR, correlate with the amplification level of the cell line, i.e. final cell lines selected in 5 nM MTX (projects 5 (d), 6 (d) and 7 (b)) have the lowest and final cell lines selected in 150 nM MTX (project 3) have the highest DHFR levels. In addition, qPCR for DHFR and Neo was carried out on genomic DNA extracted from the final cell lines or single cell clones thereof for projects 3, 4, 5 (a), 5 (d), 7 (b) and 9. The results (shown in FIG. 14B) demonstrate that lines selected in 5 nM MTX (projects 5 (d), 7 (b) and 9) have significantly lower DNA levels of DHFR and Neo—and therefore lower copy number—than lines selected in 150 nM MTX (projects 3, 4 and 5 (a)).

The results discussed above demonstrate that cell lines derived from the codon adapted ORFs (projects 5 (d), 6 (d), 7 (b) and 9 for this example) have lower gene copy number compared to lines derived from non adapted ORFs (projects 2, 3, 4, 5 (a) for this example). The use of codon adapted ORFs (CAI>0.9) therefore results in the generation of cell lines (when compared to cell lines derived from the non-adapted ORFs) with equal or higher titres, with lower levels of amplification and lower copy number of transfected DNA. The generation of clones making equivalent or higher levels of antibody from lower copy number, less amplified expression vectors is highly desirable. For example it has been shown that repeat-induced gene silencing (RIGS) can be induced when copy number of an integrated expression vector is increased and that such RIGS can then result in reduced expression levels from such vectors in mammalian cells (eg see McBurney M W et al Exp Cell Res 2002 274:1-8).

FIG. 14 (A). Plot of mean fluorescence observed for the final cell line for each of projects 2, 3, 4, 5(d), 6(d) and 7(b). The staining of cells for DHFR was undertaken as described in materials and methods, Example 1. (B) Levels of DHFR and Neo DNA by qPCR on genomic DNA from final cell lines for projects 3, 4, 5(a), 5(d), 7(b) and 9. The qPCR was performed as described in Materials and Methods, Example 1. To benchmark levels observed, the lowest values (seen in Project 7 (b)) for DHFR and Neo were set to 1 then all other values were plotted as relative fold-increase above these. Also indicated below each value is whether the protein expressed by the cell line analysed is from an ORF with CAI>0.9 (Y=Yes and N=No) and the levels of MTX required to generate the cell line (in nM MTX).

Sequence Listing

| SEQ ID NO. | DESCRIPTION OF SEQUENCE |
| --- | --- |
| 1 | 18S RNA probe - nucleotide |
| 2 | Primer 1 |
| 3 | Primer 2: |
| 4 | Heavy Chain probe: |
| 5 | Primer 1: |
| 6 | Primer 2: |
| 7 | Light chain probe |
| 8 | Primer 1: |
| 9 | Primer 2: |
| 10 | Non-adapted heavy chain of project 5 with a CAI score of 0.809 and employed in project 5(a) |
| 11 | Non-adapted light chain of project 5 with a CAI score of 0.761 and employed in project 5(a) |
| 12 | Heavy Chain ORF of project 5 with increased CAI score (0.847): See Table 5 and FIG. 6. This sequence was employed in Project 5 (b) |
| 13 | Light Chain ORF of project 5 with increased CAI score (0.833): See Table 5 and FIG. 6 This sequence was employed in project 5 (b) |
| 14 | Heavy Chain ORF of project 5 with increased CAI score (0.872). This sequence was employed in antibody project 5 (c). |
| 15 | Light Chain ORF of project 5 with increased CAI score (0.894). This sequence was employed in antibody project 5 (c). |
| 16 | Heavy Chain ORF of project 5 with increased CAI score (0.982). This sequence was employed in antibody project 5 (d). |
| 17 | Light Chain ORF of project 5 with increased CAI score (0.976). This sequence was employed in antibody project 5 (d). |
| 18 | candidate (H2L1) heavy chain |
| 19 | candidate (H2L1) light chain |
| 20 | Primer 1: |
| 21 | Primer 2: |
| 22 | DHFR Probe: |
| 23 | Primer 1: |
| 24 | Primer 2 |
| 25 | Neo Probe: |

SEQ ID NO. 1
5-VIC-tggctgaacgccacttgtccctctaaa-TAMRA-3'.

SEQ ID NO. 2
5'-aggaattgacggaagggcac-3'.

SEQ ID NO. 3
5'-ggacatctaagggcatcaca-3'

SEQ ID NO. 4
5'-FAM-ctccggctgcccattgctctcc-TAMRA-3'.

SEQ ID NO. 5
5'-ggaggcgtggtcttgtagttg-3'.

SEQ ID NO. 6
5'-ggcttctatcccagcgacatc-3'.

SEQ ID NO. 7
5'-FAM-tctcgtagtctgctttgctcagcgtca-TAMRA-3'.

SEQ ID NO. 8
5'-cttcgcaggcgtagactttgt-3'.

SEQ ID NO. 9
5'-gccctccaatcgggtaactc-3

SEQ ID NO. 10
ATGGAGTTGGGGCTGTGCTGGGTTTTCCTTGTTGCTATTTTAGAAGGTGT
CCAGTGTGAGGTGCAGCTGGTGGAGTCTGGGGGAGGCTTGGTACAGCCTG
GGGGGTCCCTGAGACTCTCCTGTGCAGTCTCTGGATTCACCTTCAGTGAC
AACGGAATGGCGTGGGTCCGCCAGGCTCCAGGGAAGGGGCTGGAGTGGGT
TTCATTCATTAGTAATTTGGCATATAGTATCGACTACGCAGACACTGTGA
CGGGCCGATTCACCATCTCCAGAGACAATGCCAAGAACTCACTGTATCTG
CAAATGAACAGCCTGAGAGCCGAGGACACGGCTGTGTATTACTGTGTCAG
CGGGACCTGGTTTGCTTACTGGGGCCAGGGCACACTAGTCACAGTCTCCT
CAGCCTCCACCAAGGGCCCATCGGTCTTCCCCCTGGCACCCTCCTCCAAG
AGCACCTCTGGGGGCACAGCGGCCCTGGGCTGCCTGGTCAAGGACTACTT
CCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGC
AGCGTGGTGACCGTGCCCTCCAGCAGCTTGGGCACCCAGACCTACATCTG
CAACGTGAATCACAAGCCCAGCAACACCAAGGTGGACAAGAAAGTTGAGC
CCAAATCTTGTGACAAAACTCACACATGCCCACCGTGCCCAGCACCTGAA
CTCGCGGGGGCACCGTCAGTCTTCCTCTTCCCCCCAAAACCCAAGGACAC
CCTCATGATCTCCCGGACCCCTGAGGTCACATGCGTGGTGGTGGACGTGA
GCCACGAAGACCCTGAGGTCAAGTTCAACTGGTACGTGGACGGCGTGGAG
GTGCATAATGCCAAGACAAAGCCGCGGGAGGAGCAGTACAACAGCACGTA
CCGTGTGGTCAGCGTCCTCACCGTCCTGCACCAGGACTGGCTGAATGGCA
AGGAGTACAAGTGCAAGGTCTCCAACAAAGCCCTCCCAGCCCCCATCGAG
AAAACCATCTCCAAAGCCAAAGGGCAGCCCCGAGAACCACAGGTGTACAC
CCTGCCCCCATCCCGGGATGAGCTGACCAAGAACCAGGTCAGCCTGACCT
GCCTGGTCAAAGGCTTCTATCCCAGCGACATCGCCGTGGAGTGGGAGAGC
AATGGGCAGCCGGAGAACAACTACAAGACCACGCCTCCCGTGCTGGACTC
CGACGGCTCCTTCTTCCTCTACAGCAAGCTCACCGTGGACAAGAGCAGGT
GGCAGCAGGGGAACGTCTTCTCATGCTCCGTGATGCATGAGGCTCTGCAC
AACCACTACACGCAGAAGAGCCTCTCCCTGTCTCCGGGTAAA

SEQ ID NO. 11
ATGAGGCTCCCTGCTCAGCTCCTGGGGCTGCTAATGCTCTGGGTCTCTGG
ATCCAGTGGGGATATTGTGATGACTCAGTCTCCACTCTCCCTGCCCGTCA
CCCCTGGAGAGCCGGCCTCCATCTCCTGCAGAGTTAGTCAGAGCCTTTTA
CACAGTAATGGATACACCTATTTACATTGGTACCTGCAGAAGCCAGGGCA
GTCTCCACAGCTCCTGATCTATAAAGTTTCCAACCGATTTTCTGGGGTCC
CTGACAGGTTCAGTGGCAGTGGATCAGGCACAGATTTTACACTGAAAATC
AGCAGAGTGGAGGCTGAGGATGTTGGGGTTTATTACTGCTCTCAAACTAG
ACATGTTCCGTACACGTTCGGCGGAGGGACCAAGGTGGAAATCAAACGTA

CGGTGGCTGCACCATCTGTCTTCATCTTCCCGCCATCTGATGAGCAGTTG
AAATCTGGAACTGCCTCTGTTGTGTGCCTGCTGAATAACTTCTATCCCAG
AGAGGCCAAAGTACAGTGGAAGGTGGACAACGCCCTCCAATCGGGTAACT
CCCAGGAGAGTGTCACAGAGCAGGACAGCAAGGACAGCACCTACAGCCTC
AGCAGCACCCTGACGCTGAGCAAAGCAGACTACGAGAAACACAAAGTCTA
CGCCTGCGAAGTCACCCATCAGGGCCTGAGCTCGCCCGTCACAAAGAGCT
TCAACAGGGGAGAGTGT

SEQ ID NO. 12
ATGGAGCTCGGGCTGTGCTGGGTGTTCCTCGTGGCCATCCTGGAGGGAGT
GCAGTGTGAGGTGCAGCTGGTGGAGAGTGGGGGCGGCCTGGTGCAGCCCG
GCGGCAGCCTGCGGCTGTCGTGCGCCGTGAGCGGCTTCACCTTCAGTGAC
AACGGCATGGCTTGGGTCAGGCAGGCCCCCGGAAAGGGGCTCGAGTGGGT
GAGCTTCATCAGTAACCTGGCCTACAGTATCGACTATGCTGACACCGTGA
CCGGCCGCTTCACTATCTCTCGGGATAATGCTAAGAACAGCCTGTACCTC
CAGATGAACAGCCTGCGCGCTGAGGACACCGCCGTGTACTACTGCGTGTC
TGGAACCTGGTTCGCCTACTGGGGCCAGGGTACACTAGTCACAGTCTCCT
CAGCCTCCACCAAGGGCCCATCGGTCTTCCCCCTGGCACCCTCCTCCAAG
AGCACCTCTGGGGGCACAGCGGCCCTGGGCTGCCTGGTCAAGGACTACTT
CCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGC
AGCGTGGTGACCGTGCCCTCCAGCAGCTTGGGCACCCAGACCTACATCTG
CAACGTGAATCACAAGCCCAGCAACACCAAGGTGGACAAGAAAGTTGAGC
CCAAATCTTGTGACAAAACTCACACATGCCCACCGTGCCCAGCACCTGAA
CTCGCGGGGGCACCGTCAGTCTTCCTCTTCCCCCCAAAACCCAAGGACAC
CCTCATGATCTCCCGGACCCCTGAGGTCACATGCGTGGTGGTGGACGTGA
GCCACGAAGACCCTGAGGTCAAGTTCAACTGGTACGTGGACGGCGTGGAG
GTGCATAATGCCAAGACAAAGCCGCGGGAGGAGCAGTACAACAGCACGTA
CCGTGTGGTCAGCGTCCTCACCGTCCTGCACCAGGACTGGCTGAATGGCA
AGGAGTACAAGTGCAAGGTCTCCAACAAAGCCCTCCCAGCCCCCATCGAG
AAAACCATCTCCAAAGCCAAAGGGCAGCCCCGAGAACCACAGGTGTACAC
CCTGCCCCCATCCCGGGATGAGCTGACCAAGAACCAGGTCAGCCTGACCT
GCCTGGTCAAAGGCTTCTATCCCAGCGACATCGCCGTGGAGTGGGAGAGC
AATGGGCAGCCGGAGAACAACTACAAGACCACGCCTCCCGTGCTGGACTC
CGACGGCTCCTTCTTCCTCTACAGCAAGCTCACCGTGGACAAGAGCAGGT
GGCAGCAGGGGAACGTCTTCTCATGCTCCGTGATGCATGAGGCTCTGCAC
AACCACTACACGCAGAAGAGCCTCTCCCTGTCTCCGGGTAAA

SEQ ID NO. 13
ATGCGCCTGCCTGCCCAGCTGCTCGGCCTGCTGATGCTGTGGGTGTCGGG
CAGCTCCGGCGACATCGTCATGACCCAGAGCCCCCTGAGTCTCCCCGTCA
CCCCCGGCGAACCTGCCAGCATCAGCTGCAGGGTGTCCCAGTCGCTGCTC
CATTCCAACGGGTACACGTACCTGCATTGGTACCTGCAGAAGCCCGGGCA
ATCCCCTCAGCTGCTGATCTACAAGGTGAGCAACCGCTTCTCCGGCGTCC

-continued

CGGACCGGTTCAGTGGCAGCGGCTCTGGAACCGACTTCACCCTGAAAATC

AGCCGCGTGGAAGCTGAGGACGTGGGCGTCTACTACTGCAGCCAGACCCG

GCATGTGCCCTACACCTTCGGCGGCGGCACAAAGGTGGAGATCAAGCGTA

CGGTGGCTGCACCATCTGTCTTCATCTTCCCGCCATCTGATGAGCAGTTG

AAATCTGGAACTGCCTCTGTTGTGTGCCTGCTGAATAACTTCTATCCCAG

AGAGGCCAAAGTACAGTGGAAGGTGGACAACGCCCTCCAATCGGGTAACT

CCCAGGAGAGTGTCACAGAGCAGGACAGCAAGGACAGCACCTACAGCCTC

AGCAGCACCCTGACGCTGAGCAAAGCAGACTACGAGAAACACAAAGTCTA

CGCCTGCGAAGTCACCCATCAGGGCCTGAGCTCGCCCGTCACAAAGAGCT

TCAACAGGGGAGAGTGT

SEQ ID NO. 14
ATGGAGCTGGGCCTGTGCTGGGTGTTCCTGGTGGCCATCCTGGAGGGCGT

GCAGTGCGAGGTGCAGCTGGTGGAGAGCGGCGGCGGCCTGGTGCAGCCCG

GCGGCAGCCTGCGCCTGAGCTGCGCCGTGAGCGGCTTCACCTTCAGCGAC

AACGGCATGGCCTGGGTGCGCCAGGCCCCCGGCAAGGGCCTGGAGTGGGT

GAGCTTCATCAGCAACCTGGCCTACAGCATCGACTACGCCGACACCGTGA

CCGGCCGCTTCACCATCAGCCGCGACAACGCCAAGAACAGCCTGTACCTG

CAGATGAACAGCCTGCGCGCCGAGGACACCGCCGTGTACTACTGCGTGAG

CGGCACCTGGTTCGCCTACTGGGGCCAGGGCACACTAGTCACAGTCTCCT

CAGCCTCCACCAAGGGCCCATCGGTCTTCCCCCTGGCACCCTCCTCCAAG

AGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCG

TGCACACCTTCCCGGCTGTCCTACAGTCCTCAGGACTCTACTCCCTCAGC

AGCGTGGTGACCGTGCCCTCCAGCAGCTTGGGCACCCAGACCTACATCTG

CAACGTGAATCACAAGCCCAGCAACACCAAGGTGGACAAGAAAGTTGAGC

CCAAATCTTGTGACAAAACTCACACATGCCCACCGTGCCCAGCACCTGAA

CTCGCGGGGCACCGTCAGTCTTCCTCTTCCCCCCAAAACCCAAGGACAC

CCTCATGATCTCCCGGACCCCTGAGGTCACATGCGTGGTGGTGGACGTGA

GCCACGAAGACCCTGAGGTCAAGTTCAACTGGTACGTGGACGGCGTGGAG

GTGCATAATGCCAAGACAAAGCCGCGGGAGGAGCAGTACAACAGCACGTA

CCGTGTGGTCAGCGTCCTCACCGTCCTGCACCAGGACTGGCTGAATGGCA

AGGAGTACAAGTGCAAGGTCTCCAACAAAGCCCTCCCAGCCCCCATCGAG

AAAACCATCTCCAAAGCCAAAGGGCAGCCCCGAGAACCACAGGTGTACAC

CCTGCCCCCATCCCGGGATGAGCTGACCAAGAACCAGGTCAGCCTGACCT

GCCTGGTCAAAGGCTTCTATCCCAGCGACATCGCCGTGGAGTGGGAGAGC

AATGGGCAGCCGGAGAACAACTACAAGACCACGCCTCCCGTGCTGGACTC

CGACGGCTCCTTCTTCCTCTACAGCAAGCTCACCGTGGACAAGAGCAGGT

GGCAGCAGGGGAACGTCTTCTCATGCTCCGTGATGCATGAGGCTCTGCAC

AACCACTACACGCAGAAGAGCCTCTCCCTGTCTCCGGGTAAA

SEQ ID NO. 15
ATGCGCCTGCCCGCCCAGCTGCTGGGCCTGCTGATGCTGTGGGTGAGCGG

CAGCAGCGGCGACATCGTGATGACCCAGAGCCCCCTGAGCCTGCCCGTGA

CCCCCGGCGAGCCCGCCAGCATCAGCTGCCGCGTGAGCCAGAGCCTGCTG

CACAGCAACGGCTACACCTACCTGCACTGGTACCTGCAGAAGCCCGGCCA

GAGCCCCCAGCTGCTGATCTACAAGGTGAGCAACCGCTTCAGCGGCGTGC

CCGACCGCTTCAGCGGCAGCGGCAGCGGCACCGACTTCACCCTGAAGATC

AGCCGCGTGGAGGCCGAGGACGTGGGCGTGTACTACTGCAGCCAGACCCG

CCACGTGCCCTACACCTTCGGCGGCGGCACCAAGGTGGAGATCAAGCGTA

CGGTGGCTGCACCATCTGTCTTCATCTTCCCGCCATCTGATGAGCAGTTG

AAATCTGGAACTGCCTCTGTTGTGTGCCTGCTGAATAACTTCTATCCCAG

AGAGGCCAAAGTACAGTGGAAGGTGGACAACGCCCTCCAATCGGGTAACT

CCCAGGAGAGTGTCACAGAGCAGGACAGCAAGGACAGCACCTACAGCCTC

AGCAGCACCCTGACGCTGAGCAAAGCAGACTACGAGAAACACAAAGTCTA

CGCCTGCGAAGTCACCCATCAGGGCCTGAGCTCGCCCGTCACAAAGAGCT

TCAACAGGGGAGAGTGT

SEQ ID NO. 16
ATGGAGCTGGGCCTGTGCTGGGTGTTCCTGGTGGCCATCCTGGAGGGCGT

GCAGTGCGAGGTGCAGCTGGTGGAGTCTGGCGGCGGACTGGTGCAGCCTG

GCGGCAGCCTGAGACTGAGCTGTGCCGTGTCCGGCTTCACCTTCAGCGAC

AACGGCATGGCCTGGGTGAGGCAGGCCCCTGGCAAGGGCCTGGAGTGGGT

GTCCTTCATCAGCAACCTGGCCTACAGCATCGACTACGCCGACACCGTGA

CCGGCAGATTCACCATCAGCCGGGACAACGCCAAGAACAGCCTGTACCTG

CAGATGAACAGCCTGAGAGCCGAGGACACCGCCGTGTACTACTGTGTGAG

CGGCACCTGGTTCGCCTACTGGGGCCAGGGCACCCTGGTGACCGTGTCCA

GCGCCAGCACCAAGGGCCCCAGCGTGTTCCCCCTGGCCCCCAGCAGCAAG

AGCACCAGCGGCGGCACAGCCGCCCTGGGCTGCCTGGTGAAGGACTACTT

CCCCGAACCGGTGACCGTGTCCTGGAACAGCGGAGCCCTGACCAGCGGCG

TGCACACCTTCCCCGCCGTGCTGCAGAGCAGCGGCCTGTACAGCCTGAGC

AGCGTGGTGACCGTGCCCAGCAGCAGCCTGGGCACCCAGACCTACATCTG

TAACGTGAACCACAAGCCCAGCAACACCAAGGTGGACAAGAAGGTGGAGC

CCAAGAGCTGTGACAAGACCCACACCTGCCCCCCCTGCCCTGCCCCCGAG

CTGGCCGGAGCCCCAGCGTGTTCCTGTTCCCCCCCAAGCCTAAGGACAC

CCTGATGATCAGCAGAACCCCCGAGGTGACCTGTGTGGTGGTGGATGTGA

GCCACGAGGACCCTGAGGTGAAGTTCAACTGGTACGTGGACGGCGTGGAG

GTGCACAATGCCAAGACCAAGCCCAGGGAGGAGCAGTACAACAGCACCTA

CCGGGTGGTGTCCGTGCTGACCGTGCTGCACCAGGATTGGCTGAACGGCA

AGGAGTACAAGTGTAAGGTGTCCAACAAGGGCCTGCCTGCCCCTATCGAG

AAAACCATCAGCAAGGCCAAGGGCCAGCCCAGAGAGCCCCAGGTGTACAC

CCTGCCCCCTAGCAGAGATGAGCTGACCAAGAACCAGGTGTCCCTGACCT

GCCTGGTGAAGGGCTTCTACCCCAGCGACATCGCCGTGGAGTGGGAGAGC

AACGGCCAGCCCGAGAACAACTACAAGACCACCCCCCCTGTGCTGGACAG
CGATGGCAGCTTCTTCCTGTACAGCAAGCTGACCGTGGACAAGAGCAGAT
GGCAGCAGGGCAACGTGTTCAGCTGCTCCGTGATGCACGAGGCCCTGCAC
AATCACTACACCCAGAAGAGCCTGAGCCTGTCCCTGGCAAG

SEQ ID NO. 17
ATGAGACTGCCCGCCCAGCTGCTGGGCCTGCTGATGCTGTGGGTGTCCGG
CAGCAGCGGCGACATCGTGATGACCCAGAGCCCCCTGAGCCTGCCCGTGA
CCCCTGGCGAGCCCGCCAGCATCAGCTGTAGAGTGAGCCAGAGCCTGCTG
CACAGCAACGGCTACACCTACCTGCACTGGTATCTGCAGAAGCCTGGCCA
GAGCCCTCAGCTGCTGATCTACAAGGTGTCCAACCGGTTCAGCGGCGTGC
CTGATAGATTCAGCGGCAGCGGCTCCGGCACCGACTTCACCCTGAAGATC
AGCAGAGTGGAGGCCGAGGATGTGGGCGTGTACTACTGCTCCCAGACCAG
ACACGTGCCTTACACCTTTGGCGGCGGAACAAAGGTGGAGATCAAGCGTA
CGGTGGCCGCCCCCAGCGTGTTCATCTTCCCCCCCAGCGATGAGCAGCTG
AAGAGCGGCACCGCCAGCGTGGTGTGTCTGCTGAACAACTTCTACCCCCG
GGAGGCCAAGGTGCAGTGGAAGGTGGACAATGCCCTGCAGAGCGGCAACA
GCCAGGAGAGCGTGACCGAGCAGGACAGCAAGGACTCCACCTACAGCCTG
AGCAGCACCCTGACCCTGAGCAAGGCCGACTACGAGAAGCACAAGGTGTA
CGCCTGTGAGGTGACCCACCAGGGCCTGTCCAGCCCCGTGACCAAGAGCT
TCAACCGGGGCGAGTGC

SEQ ID NO 18
EVQLVESGGGLVQPGGSLRLSCAVSGFTFSDNGMAWVRQAPGKGLEWVSF
ISNLAYSIDYADTVTGRFTISRDNAKNSLYLQMNSLRAEDTAVYYCVSGT
WFAYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNV
NHKPSNTKVDKKVEPKSCDKTHTCPPCPAPELAGAPSVFLFPPKPKDTLM
ISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

SEQ ID NO 19
DIVMTQSPLSLPVTPGEPASISCRVSQSLLHSNGYTYLHWYLQKPGQSPQ
LLIYKVSNRFSGVPDRFSGSGSGTDFTLKISRVEAEDVGVYYCSQTRHVP
YTFGGGTKVEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

SEQ ID NO 20
GAGGCAGTTCTGTTTACCAGGAA

SEQ ID NO 21
CCTGCATGATCCTTGTCACAA

SEQ ID NO 22
Cy5-CCATGAATCAACCAGGCCACCTCAG-BBq

SEQ ID NO 23
GCCCGGTTCTTTTTGTCAAG

SEQ ID NO 24
CTGCCTCGTCCTGCAGTTC

SEQ ID NO 25
Cy5-CCGACCTGTCCGGTGCCCTG-BBq

---

The invention claimed is:

1. A Chinese Hamster Ovarian (CHO) cell line producing at least one therapeutic protein produced by a method comprising the steps of:
   (a) transforming a CHO cell line with a polynucleotide sequence comprising (i) a sequence that encodes the therapeutic protein and has a codon adaptation index (CAI) that is equal to or greater than 0.9 as calculated using EMBOSS codon usage table Ehum.cut, and (ii) a sequence that encodes an amplifiable selection marker which is capable of providing amplification of the polynucleotide sequence;
   (b) providing at least one round of amplification in the presence of a selection agent at a concentration of 50% or less than is required to achieve a cell production yield of 0.3-1.5 g/L of the heterologous therapeutic protein in extended unfed batch culture and/or a cell productivity of 10-100 pg/cell/day of the heterologous therapeutic protein in unfed batch culture, compared with a CHO cell line with a sequence that encodes the therapeutic protein and has a codon adaptation index that is less than 0.9 as calculated using EMBOSS codon usage table Ehum.cut; and
   (c) selecting the cell line once the cell productivity and/or cell production yield of the therapeutic protein is reached; wherein the CHO cell line has lower levels of the amplifiable selection and amplification marker and copy number of transformed DNA compared to said cell line with a sequence that encodes the therapeutic protein and has a codon adaptation index that is less than 0.9 and is not provided with at least one round of amplification in the presence of a selection agent in accordance with step (b).

2. The CHO cell line of claim 1 comprising a vector comprising at least one expression cassette containing an open reading frame containing the polynucleotide sequence that encodes a therapeutic protein with a CAI score above 0.9, and a second expression cassette containing an amplifiable selection marker.

3. The CHO cell line of claim 1 comprising an amplified expression cassette containing an open reading frame containing the polynucleotide sequence that encodes a therapeutic protein with a CAI score above 0.9 contained within said cell line where it is operatively linked to a second expression cassette containing an amplifiable selection marker.

4. The CHO cell line of claim 1 wherein the cell productivity of the therapeutic protein is in the range of 10-100 pg/cell/day in an unfed batch culture.

5. The CHO cell line of claim 1, wherein the therapeutic protein is an antibody with a heavy chain, and the cell line produces an antibody composition comprising less than or equal to 5% of Non-glycosylated heavy chain.

6. The CHO cell line of claim 1, wherein the therapeutic protein is an antibody with a heavy chain, and the cell line produces an antibody composition comprising at least 95% glycosylated heavy chain.

7. The CHO cell line of claim 1, wherein the therapeutic protein is an antibody with a heavy chain, and the cell line produces an antibody composition comprising at least 96% glycosylated heavy chain.

8. The CHO cell line of claim 1, wherein the therapeutic protein is an antibody with a heavy chain, and the cell line produces an antibody composition comprising at least 97% glycosylated heavy chain.

9. The CHO cell line of claim 1, wherein the therapeutic protein is an antibody with a heavy chain, and the cell line produces an antibody composition comprising at least 98% glycosylated heavy chain.

10. The CHO cell line of claim 1, wherein the therapeutic protein is an antibody and the antibody is monoclonal.

* * * * *

SEQUENCE LISTING

<160> NUMBER OF SEQ ID NOS: 29

<210> SEQ ID NO 1
<211> LENGTH: 27
<212> TYPE: DNA
<213> ORGANISM: Artificial Sequence
<220> FEATURE:
<223> OTHER INFORMATION: Primer/Probe

<400> SEQUENCE: 1
tggctgaacg ccacttgtcc ctctaaa                              27

<210> SEQ ID NO 2
<211> LENGTH: 20
<212> TYPE: DNA
<213> ORGANISM: Artificial Sequence
<220> FEATURE:
<223> OTHER INFORMATION: Primer/Probe

<400> SEQUENCE: 2
aggaattgac ggaagggcac                                       20

<210> SEQ ID NO 3
<211> LENGTH: 20
<212> TYPE: DNA
<213> ORGANISM: Artificial Sequence
<220> FEATURE:

<223> OTHER INFORMATION: Primer/Probe

<400> SEQUENCE: 3
ggacatctaa gggcatcaca                                               20

<210> SEQ ID NO 4
<211> LENGTH: 22
<212> TYPE: DNA
<213> ORGANISM: Artificial Sequence
<220> FEATURE:
<223> OTHER INFORMATION: Primer/Probe

<400> SEQUENCE: 4
ctccggctgc ccattgctct cc                                            22

<210> SEQ ID NO 5
<211> LENGTH: 21
<212> TYPE: DNA
<213> ORGANISM: Artificial Sequence
<220> FEATURE:
<223> OTHER INFORMATION: Primer/Probe

<400> SEQUENCE: 5
ggaggcgtgg tcttgtagtt g                                             21

<210> SEQ ID NO 6
<211> LENGTH: 21
<212> TYPE: DNA
<213> ORGANISM: Artificial Sequence
<220> FEATURE:
<223> OTHER INFORMATION: Primer/Probe

<400> SEQUENCE: 6
ggcttctatc ccagcgacat c                                             21

<210> SEQ ID NO 7
<211> LENGTH: 27
<212> TYPE: DNA
<213> ORGANISM: Artificial Sequence
<220> FEATURE:
<223> OTHER INFORMATION: Primer/Probe

<400> SEQUENCE: 7
tctcgtagtc tgctttgctc agcgtca                                       27

<210> SEQ ID NO 8
<211> LENGTH: 21
<212> TYPE: DNA
<213> ORGANISM: Artificial Sequence
<220> FEATURE:
<223> OTHER INFORMATION: Primer/Probe

<400> SEQUENCE: 8
cttcgcaggc gtagactttg t                                             21

<210> SEQ ID NO 9
<211> LENGTH: 20
<212> TYPE: DNA
<213> ORGANISM: Artificial Sequence
<220> FEATURE:
<223> OTHER INFORMATION: Primer/Probe

<400> SEQUENCE: 9
gccctccaat cgggtaactc                                               20

<210> SEQ ID NO 10
<211> LENGTH: 1392
<212> TYPE: DNA
<213> ORGANISM: Artificial Sequence
<220> FEATURE:
<223> OTHER INFORMATION: Heavy chain

<400> SEQUENCE: 10

| | | | | | |
|---|---|---|---|---|---|
| atggagttgg | ggctgtgctg | ggttttcctt | gttgctattt | tagaaggtgt | ccagtgtgag | 60 |
| gtgcagctgg | tggagtctgg | gggaggcttg | gtacagcctg | gggggtccct | gagactctcc | 120 |
| tgtgcagtct | ctggattcac | cttcagtgac | aacggaatgg | cgtgggtccg | ccaggctcca | 180 |
| gggaaggggc | tggagtgggt | ttcattcatt | agtaatttgg | catatagtat | cgactacgca | 240 |
| gacactgtga | cgggccgatt | caccatctcc | agagacaatg | ccaagaactc | actgtatctg | 300 |
| caaatgaaca | gcctgagagc | cgaggacacg | gctgtgtatt | actgtgtcag | cgggacctgg | 360 |
| tttgcttact | ggggccaggg | cacactagtc | acagtctcct | cagcctccac | caagggccca | 420 |
| tcggtcttcc | ccctggcacc | ctcctccaag | agcacctctg | gggcacagc | ggccctgggc | 480 |
| tgcctggtca | aggactactt | ccccgaaccg | gtgacggtgt | cgtggaactc | aggcgccctg | 540 |
| accagcggcg | tgcacacctt | cccggctgtc | ctacagtcct | caggactcta | ctccctcagc | 600 |
| agcgtggtga | ccgtgccctc | cagcagcttg | ggcacccaga | cctacatctg | caacgtgaat | 660 |
| cacaagccca | gcaacaccaa | ggtggacaag | aaagttgagc | ccaaatcttg | tgacaaaact | 720 |
| cacacatgcc | caccgtgccc | agcacctgaa | ctcgcggggg | gaccgtcagt | cttcctcttc | 780 |
| cccccaaaac | ccaaggacac | cctcatgatc | tcccggaccc | ctgaggtcac | atgcgtggtg | 840 |
| gtggacgtga | gccacgaaga | ccctgaggtc | aagttcaact | ggtacgtgga | cggcgtggag | 900 |
| gtgcataatg | ccaagacaaa | gccgcgggag | gagcagtaca | acagcacgta | ccgtgtggtc | 960 |
| agcgtcctca | ccgtcctgca | ccaggactgg | ctgaatggca | aggagtacaa | gtgcaaggtc | 1020 |
| tccaacaaag | ccctcccagc | ccccatcgag | aaaaccatct | ccaaagccaa | agggcagccc | 1080 |
| cgagaaccac | aggtgtacac | cctgcccca | tcccgggatg | agctgaccaa | gaaccaggtc | 1140 |
| agcctgacct | gcctggtcaa | aggcttctat | cccagcgaca | tcgccgtgga | gtgggagagc | 1200 |
| aatgggcagc | cggagaacaa | ctacaagacc | acgcctcccg | tgctggactc | cgacggctcc | 1260 |
| ttcttcctct | acagcaagct | caccgtggac | aagagcaggt | ggcagcaggg | gaacgtcttc | 1320 |
| tcatgctccg | tgatgcatga | ggctctgcac | aaccactaca | cgcagaagag | cctctccctg | 1380 |
| tctccgggta | aa | | | | | 1392 |

<210> SEQ ID NO 11
<211> LENGTH: 717
<212> TYPE: DNA
<213> ORGANISM: Artificial Sequence
<220> FEATURE:
<223> OTHER INFORMATION: Light chain

<400> SEQUENCE: 11

| | | | | | |
|---|---|---|---|---|---|
| atgaggctcc | ctgctcagct | cctggggctg | ctaatgctct | gggtctctgg | atccagtggg | 60 |
| gatattgtga | tgactcagtc | tccactctcc | ctgcccgtca | cccctggaga | gccggcctcc | 120 |
| atctcctgca | gagttagtca | gagccttttta | cacagtaatg | gatacaccta | tttacattgg | 180 |
| tacctgcaga | agccagggca | gtctccacag | ctcctgatct | ataaagtttc | caaccgattt | 240 |
| tctggggtcc | ctgacaggtt | cagtggcagt | ggatcaggca | cagatttac | actgaaaatc | 300 |
| agcagagtgg | aggctgagga | tgttgggggtt | tattactgct | ctcaaactag | acatgttccg | 360 |

| | |
|---|---|
| tacacgttcg gcggagggac caaggtggaa atcaaacgta cggtggctgc accatctgtc | 420 |
| ttcatcttcc cgccatctga tgagcagttg aaatctggaa ctgcctctgt tgtgtgcctg | 480 |
| ctgaataact tctatcccag agaggccaaa gtacagtgga aggtggacaa cgccctccaa | 540 |
| tcgggtaact cccaggagag tgtcacagag caggacagca aggacagcac ctacagcctc | 600 |
| agcagcaccc tgacgctgag caaagcagac tacgagaaac acaaagtcta cgcctgcgaa | 660 |
| gtcacccatc agggcctgag ctcgcccgtc acaaagagct tcaacagggg agagtgt | 717 |

<210> SEQ ID NO 12
<211> LENGTH: 1392
<212> TYPE: DNA
<213> ORGANISM: Artificial Sequence
<220> FEATURE:
<223> OTHER INFORMATION: Codon adapted Heavy chain

<400> SEQUENCE: 12

| | |
|---|---|
| atggagctcg gctgtgctg ggtgttcctc gtggccatcc tggagggagt gcagtgtgag | 60 |
| gtgcagctgg tggagagtgg gggcggcctg gtgcagcccg gcggcagcct gcggctgtcg | 120 |
| tgcgccgtga gcggcttcac cttcagtgac aacggcatgg cttgggtcag gcaggccccc | 180 |
| ggaaagggc tcgagtgggt gagcttcatc agtaacctgg cctacagtat cgactatgct | 240 |
| gacaccgtga ccggccgctt cactatctct cgggataatg ctaagaacag cctgtacctc | 300 |
| cagatgaaca gcctgcgcgc tgaggacacc gccgtgtact actgcgtgtc tggaacctgg | 360 |
| ttcgcctact ggggccaggg tacactagtc acagtctcct cagcctccac caagggccca | 420 |
| tcggtcttcc cctggcacc ctcctccaag agcacctctg gggcacagc ggccctgggc | 480 |
| tgcctggtca aggactactt ccccgaaccg gtgacggtgt cgtggaactc aggcgccctg | 540 |
| accagcggcg tgcacacctt cccggctgtc ctacagtcct caggactcta ctccctcagc | 600 |
| agcgtggtga ccgtgccctc agcagcttg gcacccaga cctacatctg caacgtgaat | 660 |
| cacaagccca gcaacaccaa ggtggacaag aaagttgagc ccaaatcttg tgacaaaact | 720 |
| cacacatgcc caccgtgccc agcacctgaa ctcgcggggg gaccgtcagt cttcctcttc | 780 |
| cccccaaaac ccaaggacac cctcatgatc tcccggaccc ctgaggtcac atgcgtggtg | 840 |
| gtggacgtga gccacgaaga ccctgaggtc aagttcaact ggtacgtgga cggcgtggag | 900 |
| gtgcataatg ccaagacaaa gccgcgggag gagcagtaca acagcacgta ccgtgtggtc | 960 |
| agcgtcctca ccgtcctgca ccaggactgg ctgaatggca aggagtacaa gtgcaaggtc | 1020 |
| tccaacaaag ccctcccagc ccccatcgag aaaaccatct ccaaagccaa agggcagccc | 1080 |
| cgagaaccac aggtgtacac cctgcccca tcccgggatg agctgaccaa gaaccaggtc | 1140 |
| agcctgacct gcctggtcaa aggcttctat cccagcgaca tcgccgtgga gtgggagagc | 1200 |
| aatgggcagc cggagaacaa ctacaagacc acgcctcccg tgctggactc cgacggctcc | 1260 |
| ttcttcctct acagcaagct caccgtggac aagagcaggt ggcagcaggg gaacgtcttc | 1320 |
| tcatgctccg tgatgcatga ggctctgcac aaccactaca cgcagaagag cctctccctg | 1380 |
| tctccgggta aa | 1392 |

<210> SEQ ID NO 13
<211> LENGTH: 717
<212> TYPE: DNA
<213> ORGANISM: Artificial Sequence
<220> FEATURE:
<223> OTHER INFORMATION: Codon adapted Light chain

<400> SEQUENCE: 13

```
atgcgcctgc ctgcccagct gctcggcctg ctgatgctgt gggtgtcggg cagctccggc    60
gacatcgtca tgacccagag ccccctgagt ctccccgtca cccccggcga acctgccagc   120
atcagctgca gggtgtccca gtcgctgctc cattccaacg ggtacacgta cctgcattgg   180
tacctgcaga agcccgggca atcccctcag ctgctgatct acaaggtgag caaccgcttc   240
tccggcgtcc cggaccggtt cagtggcagc ggctctggaa ccgacttcac cctgaaaatc   300
agccgcgtgg aagctgagga cgtgggcgtc tactactgca gccagaccccg gcatgtgccc   360 tacaccttcg gcggcggcac aaaggtggag atcaagcgta cggtggctgc accatctgtc   420
ttcatcttcc cgccatctga tgagcagttg aaatctggaa ctgcctctgt tgtgtgcctg   480
ctgaataact tctatcccag agaggccaaa gtacagtgga aggtggacaa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct caacagggg agagtgt     717
```

<210> SEQ ID NO 14
<211> LENGTH: 1392
<212> TYPE: DNA
<213> ORGANISM: Artificial Sequence
<220> FEATURE:
<223> OTHER INFORMATION: Codon adapted Heavy chain

<400> SEQUENCE: 14

```
atggagctgg gcctgtgctg ggtgttcctg gtggccatcc tggagggcgt gcagtgcgag    60
gtgcagctgg tggagagcgg cggcggcctg gtgcagcccg gcggcagcct cgcgcctgagc   120 tgcgccgtga gcggcttcac cttcagcgac aacggcatgg cctgggtgcg ccaggcccccc   180 ggcaagggcc tggagtgggt gagcttcatc agcaacctgg cctacagcat cgactacgcc   240
gacaccgtga ccggccgctt caccatcagc cgcgacaacg ccaagaacag cctgtacctg   300
cagatgaaca gcctgcgcgc cgaggacacc gccgtgtact actgcgtgag cggcacctgg   360
ttcgcctact ggggccaggg cacactagtc acagtctcct cagcctccac caagggccca   420
tcggtcttcc ccctggcacc ctcctccaag agcacctctg gggcacagc ggccctgggc   480 tgcctggtca aggactactt ccccgaaccg gtgacggtgt cgtggaactc aggcgccctg   540
accagcggcg tgcacacctt cccggctgtc ctacagtcct caggactcta ctccctcagc   600
agcgtggtga ccgtgccctc agcagcttg ggcacccaga cctacatctg caacgtgaat   660
cacaagccca gcaacaccaa ggtggacaag aaagttgagc ccaaatcttg tgacaaaact   720
cacacatgcc caccgtgccc agcacctgaa ctcgcggggg gaccgtcagt cttcctcttc   780
cccccaaaaa ccaaggacac cctcatgatc tccccggaccc ctgaggtcac atgcgtggtg   840
gtggacgtga gccacgaaga ccctgaggtc aagttcaact ggtacgtgga cggcgtggag   900
gtgcataatg ccaagacaaa gccgcgggag gagcagtaca acagcacgta ccgtgtggtc   960
agcgtcctca ccgtcctgca ccaggactgg ctgaatggca aggagtacaa gtgcaaggtc  1020
tccaacaaag ccctcccagc ccccatcgag aaaaccatct ccaaagccaa agggcagccc  1080
cgagaaccac aggtgtacac cctgccccca tcccgggatg agctgaccaa gaaccaggtc  1140
agcctgacct gcctggtcaa aggcttctat cccagcgaca tcgccgtgga gtgggagagc  1200
aatgggcagc cggagaacaa ctacaagacc acgcctcccg tgctggactc cgacggctcc  1260
ttcttcctct acagcaagct caccgtggac aagagcaggt ggcagcaggg gaacgtcttc  1320
```

```
tcatgctccg tgatgcatga ggctctgcac aaccactaca cgcagaagag cctctccctg    1380
tctccgggta aa                                                        1392

<210> SEQ ID NO 15
<211> LENGTH: 717
<212> TYPE: DNA
<213> ORGANISM: Artificial Sequence
<220> FEATURE:
<223> OTHER INFORMATION: Codon adapted Light chain

<400> SEQUENCE: 15
atgcgcctgc cgcccagct gctgggcctg ctgatgctgt gggtgagcgg cagcagcggc      60
gacatcgtga tgacccagag ccccctgagc ctgcccgtga ccccggcga gcccgccagc     120 atcagctgcc gcgtgagcca gagcctgctg cacagcaacg gctacaccta cctgcactgg     180
tacctgcaga gcccggcca gagcccccag ctgctgatct acaaggtgag caaccgcttc     240
agcggcgtgc cgaccgctt cagcggcagc ggcagcggca ccgacttcac cctgaagatc     300
agccgcgtgg aggccgagga cgtgggcgtg tactactgca gccagaccg ccacgtgccc     360 tacaccttcg gcggcggcac caaggtggag atcaagcgta cggtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggacaa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgt       717

<210> SEQ ID NO 16
<211> LENGTH: 1392
<212> TYPE: DNA
<213> ORGANISM: Artificial Sequence
<220> FEATURE:
<223> OTHER INFORMATION: Codon adapted Heavy chain

<400> SEQUENCE: 16
atggagctgg gcctgtgctg ggtgttcctg gtggccatcc tggagggcgt gcagtgcgag      60
gtgcagctgg tggagtctgg cggcggactg gtgcagcctg gcggcagcct gagactgagc     120
tgtgccgtgt ccggcttcac cttcagcgac aacggcatgg cctgggtgag caggccccct     180
ggcaagggcc tggagtgggt gtccttcatc agcaacctgg cctacagcat cgactacgcc     240
gacaccgtga ccggcagatt caccatcagc cgggacaacg ccaagaacag cctgtacctg     300
cagatgaaca gcctgagagc cgaggacacc gccgtgtact actgtgtgag cggcacctgg     360
ttcgcctact ggggccaggg caccctggtg accgtgtcca gcgccagcac caagggcccc     420
agcgtgttcc ccctggcccc cagcagcaag agcaccagcg gcggcacagc cgccctgggc     480
tgcctggtga aggactactt ccccgaaccg gtgaccgtgt cctggaacag cggagccctg     540
accagcggcg tgcacacctt ccccgccgtg ctgcagagca gcggcctgta cagcctgagc     600
agcgtggtga ccgtgcccag cagcagcctg ggcacccaga cctacatctg taacgtgaac     660
cacaagccca gcaacaccaa ggtggacaag aaggtggagc ccaagagctg tgacaagacc     720
cacacctgcc ccccctgccc tgccccgag ctggccggag ccccagcgt gttcctgttc     780 ccccccaagc ctaaggacac cctgatgatc agcagaaccc ccgaggtgac ctgtgtggtg     840
gtggatgtga gccacgagga ccctgaggtg aagttcaact ggtacgtgga cggcgtggag     900
gtgcacaatg ccaagaccaa gccccaggag gagcagtaca acagcaccta ccgggtggtg     960
```

```
tccgtgctga ccgtgctgca ccaggattgg ctgaacggca aggagtacaa gtgtaaggtg    1020
tccaacaagg ccctgcctgc ccctatcgag aaaaccatca gcaaggccaa gggccagccc    1080
agagagcccc aggtgtacac cctgcccct agcagagatg agctgaccaa gaaccaggtg     1140
tccctgacct gcctggtgaa gggcttctac cccagcgaca tcgccgtgga gtgggagagc    1200
aacggccagc ccgagaacaa ctacaagacc acccccctg tgctggacag cgatggcagc     1260
ttcttcctgt acagcaagct gaccgtggac aagagcagat ggcagcaggg caacgtgttc    1320
agctgctccg tgatgcacga ggccctgcac aatcactaca cccagaagag cctgagcctg    1380 tccctggca ag                                                         1392
```

<210> SEQ ID NO 17
<211> LENGTH: 717
<212> TYPE: DNA
<213> ORGANISM: Artificial Sequence
<220> FEATURE:
<223> OTHER INFORMATION: Codon adapted Light chain

<400> SEQUENCE: 17

```
atgagactgc ccgcccagct gctgggcctg ctgatgctgt gggtgtccgg cagcagcggc      60
gacatcgtga tgacccagag ccccctgagc ctgcccgtga ccctggcga gcccgccagc     120 atcagctgta gtgtgagcca gagcctgctg cacagcaacg gctacaccta cctgcactgg    180
tatctgcaga gcctggcca gagccctcag ctgctgatct acaaggtgtc caaccggttc     240
agcggcgtgc ctgatagatt cagcggcagc ggctccggca ccgacttcac cctgaagatc    300
agcagagtgg aggccgagga tgtgggcgtg tactactgct cccagaccag acacgtgcct    360 tacaccttg gcggcggaac aaaggtggag atcaagcgta cggtggccgc ccccagcgtg     420
ttcatcttcc ccccagcga tgagcagctg aagagcggca ccgccagcgt ggtgtgtctg    480
ctgaacaact tctacccccg ggaggccaag gtgcagtgga aggtggacaa tgccctgcag    540
agcggcaaca gccaggagag cgtgaccgag caggacagca aggactccac ctacagcctg    600
agcagcaccc tgaccctgag caaggccgac tacgagaagc acaaggtgta cgcctgtgag    660
gtgacccacc agggcctgtc cagccccgtg accaagagct caaccggggg cgagtgc      717
```

<210> SEQ ID NO 18
<211> LENGTH: 445
<212> TYPE: PRT
<213> ORGANISM: Artificial Sequence
<220> FEATURE:
<223> OTHER INFORMATION: H2L1 Heavy chain

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asp Asn
            20                  25                  30

Gly Met Ala Trp Val Arg Gln Ala Pro Gly Lys Gly Leu Glu Trp Val
        35                  40                  45

Ser Phe Ile Ser Asn Leu Ala Tyr Ser Ile Asp Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95
```

```
Val Ser Gly Thr Trp Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 19
<211> LENGTH: 219
<212> TYPE: PRT
<213> ORGANISM: Artificial Sequence
<220> FEATURE:
<223> OTHER INFORMATION: H2L1 light chain

<400> SEQUENCE: 19

Asp Ile Val Met Thr Gln Ser Pro Leu Ser Leu Pro Val Thr Pro Gly
1               5                   10                  15
```

Glu Pro Ala Ser Ile Ser Cys Arg Val Ser Gln Ser Leu His Ser
                20                  25                  30

Asn Gly Tyr Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Thr
                 85                  90                  95

Arg His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 20
<211> LENGTH: 23
<212> TYPE: DNA
<213> ORGANISM: Artificial Sequence
<220> FEATURE:
<223> OTHER INFORMATION: Primer/probe

<400> SEQUENCE: 20
gaggcagttc tgtttaccag gaa                                          23

<210> SEQ ID NO 21
<211> LENGTH: 21
<212> TYPE: DNA
<213> ORGANISM: Artificial Sequence
<220> FEATURE:
<223> OTHER INFORMATION: Primer/probe

<400> SEQUENCE: 21
cctgcatgat ccttgtcaca a                                            21

<210> SEQ ID NO 22
<211> LENGTH: 25
<212> TYPE: DNA
<213> ORGANISM: Artificial Sequence
<220> FEATURE:
<223> OTHER INFORMATION: DHFR probe

<400> SEQUENCE: 22
ccatgaatca accaggccac ctcag                                        25

<210> SEQ ID NO 23
<211> LENGTH: 20
<212> TYPE: DNA

<213> ORGANISM: Artificial Sequence
<220> FEATURE:
<223> OTHER INFORMATION: Primer/probe

<400> SEQUENCE: 23
gcccggttct ttttgtcaag                                               20

<210> SEQ ID NO 24
<211> LENGTH: 19
<212> TYPE: DNA
<213> ORGANISM: Artificial Sequence
<220> FEATURE:
<223> OTHER INFORMATION: Primer/probe

<400> SEQUENCE: 24
ctgcctcgtc ctgcagttc                                                19

<210> SEQ ID NO 25
<211> LENGTH: 20
<212> TYPE: DNA
<213> ORGANISM: Artificial Sequence
<220> FEATURE:
<223> OTHER INFORMATION: Primer/probe

<400> SEQUENCE: 25
ccgacctgtc cggtgccctg                                               20

<210> SEQ ID NO 26
<211> LENGTH: 48
<212> TYPE: DNA
<213> ORGANISM: Artificial Sequence
<220> FEATURE:
<223> OTHER INFORMATION: Light chain CDR1

<400> SEQUENCE: 26
agagttagtc agagccttt acacagtaat ggatacacct atttacat                 48

<210> SEQ ID NO 27
<211> LENGTH: 48
<212> TYPE: DNA
<213> ORGANISM: Artificial Sequence
<220> FEATURE:
<223> OTHER INFORMATION: Light chain CDR1

<400> SEQUENCE: 27
agggtgtccc agtcgctgct ccattccaac gggtacacgt acctgcat                48

<210> SEQ ID NO 28
<211> LENGTH: 45
<212> TYPE: DNA
<213> ORGANISM: Artificial Sequence
<220> FEATURE:
<223> OTHER INFORMATION: Light chain CDR1

<400> SEQUENCE: 28
gtgagccaga gcctgctgca cagcaacggc tacacctacc tgcac                   45

<210> SEQ ID NO 29
<211> LENGTH: 48
<212> TYPE: DNA
<213> ORGANISM: Artificial Sequence

```
<220> FEATURE:
<223> OTHER INFORMATION: Light chain CDR1

<400> SEQUENCE: 29
agagtgagcc agagcctgct gcacagcaac ggctacacct acctgcac         48
```